(12) United States Patent
Lockhart et al.

(10) Patent No.: US 8,321,148 B2
(45) Date of Patent: Nov. 27, 2012

(54) MULTIPLE COMPARTMENT DOSING MODEL

(75) Inventors: Daniel J. Lockhart, Santa Ynez, CA (US); David J. Lockhart, Del Mar, CA (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 306 days.

(21) Appl. No.: 12/604,855

(22) Filed: Oct. 23, 2009

(65) Prior Publication Data

US 2010/0106473 A1 Apr. 29, 2010

Related U.S. Application Data

(60) Provisional application No. 61/108,192, filed on Oct. 24, 2008.

(51) Int. Cl.
*G06F 19/00* (2011.01)
(52) U.S. Cl. .......................................................... 702/19
(58) Field of Classification Search ........................ None
See application file for complete search history.

(56) References Cited

U.S. PATENT DOCUMENTS

| | | | |
|---|---|---|---|
| 5,496,701 A | 3/1996 | Pollard-Knight | |
| 5,658,567 A | 8/1997 | Calhoun et al. | |
| 6,274,597 B1 | 8/2001 | Fan et al. | |
| 6,583,158 B1 | 6/2003 | Fan et al. | |
| 6,589,964 B2 | 7/2003 | Fan et al. | |
| 6,599,919 B2 | 7/2003 | Fan et al. | |
| 6,774,135 B2 | 8/2004 | Fan et al. | |
| 6,916,829 B2 | 7/2005 | Fan et al. | |
| 7,141,582 B2 | 11/2006 | Fan et al. | |
| 2002/0061540 A1 | 5/2002 | Grass et al. | |
| 2004/0039530 A1 | 2/2004 | Leesman et al. | |
| 2006/0067881 A1 | 3/2006 | Groman et al. | |
| 2006/0153829 A1 | 7/2006 | Fan | |
| 2007/0071681 A1 | 3/2007 | Gadkar et al. | |

FOREIGN PATENT DOCUMENTS

| | | |
|---|---|---|
| WO | 2008/121826 A2 | 10/2008 |
| WO | 2008/134628 A2 | 11/2008 |

OTHER PUBLICATIONS

Derendorf et al. (Pharmaceutical Research (1999) vol. 16, No. 2, pp. 176-185).*
Dayneka et al. Journal of Pharmacokinetics and Biophamaceutics (1993) vol. 21, No. 4, pp. 457-478.*
Jusko et al. Journal of Pharmacokinetics and Biophamaceutics (1995) vol. 23, No. 1, pp. 5-8.*
Krzyzanski et al.. Journal of Pharmacokinetics and Biophamaceutics (1997) vol. 25, No. 1, p. 107-123.*
U.S. Appl. No. 61/028,123, filed Feb. 12, 2008, "Treatment of Gaucher Disease with Specific Pharmacological Chaperones and Monitoring Treatment Using Surrogate Markers."
U.S. Appl. No. 61/028,141, filed Feb. 12, 2008, "Method to Predict Response to Pharmacological Chaperone Treatment of Diseases."
U.S. Appl. No. 61/035,684, filed Mar. 11, 2008, "Method to Predict Response to Pharmacological Chaperone Treatment of Diseases."
U.S. Appl. No. 61/035,866, filed Mar. 12, 2008, "Assays for Diagnosing and Evaluating Treatment Options for Pompe Disease."
U.S. Appl. No. 61/035,869, filed Mar. 12, 2008, "Treatment of Pomper Disease with Specific Pharmacological Chaperones and Monitoring Treatment Using Surrogate Markers."
U.S. Appl. No. 11/440,473, filed May 17, 2006, "A Method for the Treatment of Pompe Disease Using 1-Deoxynojirimycin and Derivatives."
U.S. Appl. No. 11/449,528, filed Jun. 8, 2006, "Treatment of CNS Disorders Associated with Mutations in Genes Encoding Lysosomal Enzymes."
U.S. Appl. No. 11/607,286, filed Dec. 1, 2006, "Combination Therapy for Treating Protein Deficiency Disorders."
U.S. Appl. No. 11/749,512, filed May 16, 2007, "Assays for Diagnosing and Evaluating Treatment Options for Fabry Disease."
U.S. Appl. No. 11/768,043, filed Jun. 25, 2007, "Method for the Treatment of Neurological Disorders by Enhancing the Activity of b-Glucocerebrosidase."
International Search Report for PCT/US2009/061892, dated Dec. 23, 2009.
Written Opinion for PCT/US2009/061892, dated Dec. 23, 2009.

* cited by examiner

*Primary Examiner* — Lori A Clow
(74) *Attorney, Agent, or Firm* — Hoffman & Baron, LLP

(57) ABSTRACT

The method for modeling a dosing regimen for a medicament includes providing a system having at least two biocompartments. The method determines steady state levels in each of the biocompartments. After that, the method provides for modifying values to calculate an amount of at least one protein in one of the biocompartments to which the protein is being transported. Next, the method calculates and integrates a weighted value of the protein to find a weighted area under the curve. Then, the method calculates and integrates a non-drug value of the protein to find a non-drug area under the curve. Finally, the method evaluates one or more dosing regimens by comparing the weighted area under the curve and the non-drug area under the curve of the protein to determine a net effect of the drug over the time period.

20 Claims, 26 Drawing Sheets

FIG. 5

☐ Two Compartment Dosing Model

Version 6.5 08/11/2009

| Model | Input | Solution Data |
|---|---|---|

Definitions

- 56 — $N_1(t)$ — Amount in compartment 1 at time t
- 58 — $N_1(0)$ — Amount in compartment 1 at time 0
- 60 — $N_2(t)$ — Amount in compartment 2 at time t
- 62 — $N_2(0)$ — Amount in compartment 2 at time 0
- 64 — $S_1$ — Synthesis rate (amount/hr) in Compartment 1
- 66 — $k_{d1}$ — Degradation rate constant (1/hr) in Compartment 1
- 68 — $k_{T12}$ — Transport rate constant (1/hr) from Compartment 1 to Compartment 2
- 70 — $k_{d2}$ — Degradation rate constant (1/hr) in Compartment 2

Pulse Parameters

- 74 — $t_{plstart}$ — Time (hr) to start the first pulse.
- 76 — $t_{pldur}$ — Duration (hrs) of each pulse.
- 78 — $t_{plint}$ — Interval (hrs) between pulses from the start of one to the start of the next.
- 80 — $n_{pl}$ — Number of times to repeat the pulse.
- 81 — $A_2$ — Enzyme Replacement Therapy rate (amount/hr) directly into Compartment 2

Assumptions:
The Degradation rates in Compartment 1 and 2 are proportional to Amounts, $N_1(t)$, $N_2(t)$. — 82
The Transport rate from Compartment 1 to 2 is proportional to the Amount in Compartment 1, $N_1(t)$ — 84

Run

| Standard | Pulse | Pre-Equilubrium | AUC Window | Drug t$_{1/2}$ | ERT | Save |

☑ Pulse 1 Active?    Copy Standard Parameters

Pulse 1 System Parameters:

64 — $S_1$ = [0.01] (amount/hrs)
66 — $k_{d1}$ = [0.03465] (1/hrs) Half life: [20] (hrs)
68 — $k_{T12}$ = [0.0693] (1/hrs) Half life: [10] (hrs)
70 — $k_{d2}$ = [0.009625] (1/hrs) Half life: [72] (hrs)

Pulse 1 Time Parameters:
Common Pulse Settings: ⊟ (click to hide)

```
Custom (enter values below)
Twice a day
Once a day
Once every other day
Once a day 1 on 6 off
Once a day 2 on 5 off
Once a day 3 on 4 off
Once a day 4 on 3 off
Once a day 7 on 7 off
Once a day 14 on 14 off
Run All Consecutively
```
—112

74 — $t_{plstart}$ = [0] (hrs)
76 — $t_{pldur}$ = [20] (hrs)
78 — $t_{plint}$ = [24] (hrs)   } 72
80 — $n_{pl}$ = [3] (hrs)

116 — ☑ Repeat Pulse 1 [8] times, every [168] (hrs)

*FIG. 7C*
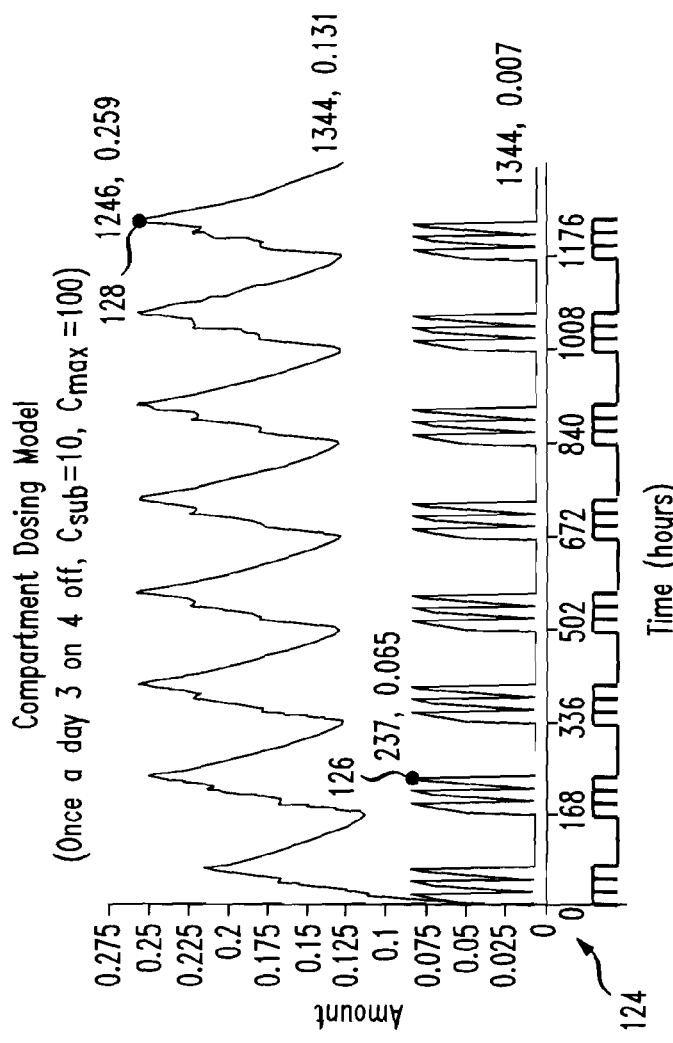
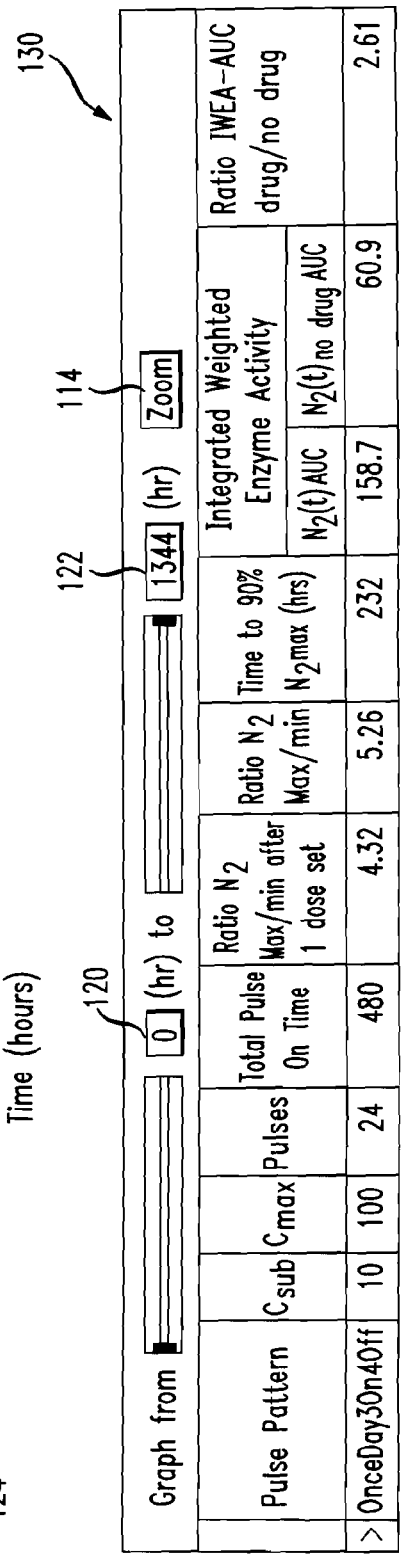

[Run]

| Standard | Pulse | Pre-Equilubrium | AUC Window | Drug $t_{1/2}$ | ERT | Save |

☑ Pulse 1 Active?   Copy Standard Parameters
Pulse 1 System Parameters:

64 — $S_1$ = [0.01] (amount/hrs)
66 — $k_{d1}$ = [0.03465] (1/hrs) Half life: [20] (hrs)
68 — $k_{T12}$ = [0.0693] (1/hrs) Half life: [10] (hrs)
70 — $k_{d2}$ = [0.009625] (1/hrs) Half life: [72] (hrs)

Pulse 1 Time Parameters:
Common Pulse Settings: ⊟ (click to hide)

74 — $t_{plstart}$ = [0] (hrs) ⎫
76 — $t_{pldur}$ = [20] (hrs) ⎬ 72
78 — $t_{plint}$ = [24] (hrs) ⎪
80 — $n_{pl}$ = [3] (hrs) ⎭

☑ Repeat Pulse 1 [2] times, every [672] (hrs)

☑ Graph Pulse 1? _-__-__-__-_

☐ Fractional Pulse Active?

$N_1$ % = [60]
$N_2$ % = [303]

[Run]

| Pre-Equilibrium Results | — 102 |
| Time     600 hrs used as t=0 | — 100 |

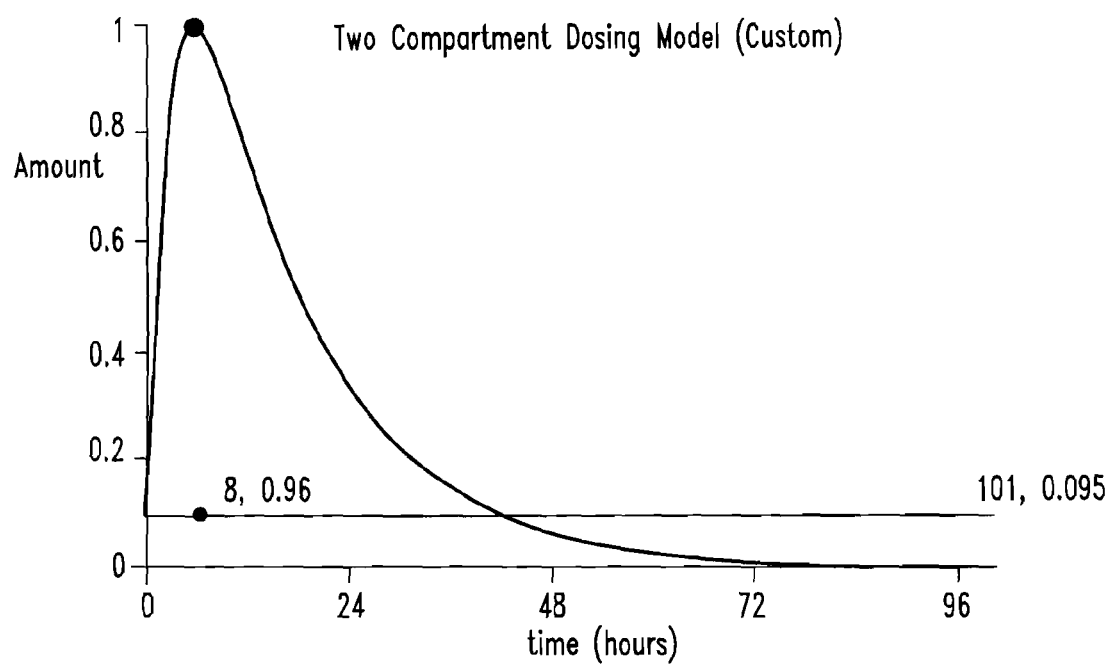

Concentration Curve Shape: ○ Exponential ● Sine² ← 170

Start = [0] (hrs) ↘ 172
Cycle Time = [24] (hrs)
$C_{min}$ = [5] % of $C_{max}$
Continue for: ● Full Time Window
○ [14] Cycles
○ [1344] (hrs)

☐ *Control pulse on/off at [1] *$K_i$?
* If checked, $K_i$ on/off overrides current Pulse 1 time parameters from the Pulse tab.

Two Compartment Dosing Model
(Custom, $C^{sub}$=10, $C^{max}$=10) ← 178

[Run]

| Standard | Pulse | Pre-Equilubrium | AUC Window | Drug $t_{1/2}$ | ERT | Save |

Intergrated Weighted Enzyme Activity

☑ Active?

Substrate concentration:

150 — $C_{Substrate}$ = [10] *$K_m$ (0.1 to 1000)

☐ Optional $C_{Substrate}(s)$ [1], [100]

Max drug concentration:

152 — $C_{max}$ = [10] *$K_i$ (0 to 1000)

☐ Constant for [4] (hrs) at $C_{max}$

Concentration Curve Shape: ⦿ Exponential ◯ Sine2

Drug elimination rate constant:

154 — $k_{drug}$ = [0.0693] (1/hrs) Half life: [10] (hrs)

Time to max drug level:

156 — $t_{rise}$ = [2 ▽] (hrs) rise to $C_{max}$

☐ *Control pulse on/off at [1] *$K_i$?

* If checked, $K_i$ on/off overrides current Pulse 1 time parameters from the Pulse tab.

Graph Options:

☐ Graph Drug Concentration $C_d(t)$? _____

☐ Graph Single Pulse $C_d(t)$? _____

☑ Graph V factor? _____

☑ Graph Weighted $N2(t)$? _____

☑ Graph Weighted $N2(t)_{no\ drug}$ — — — — —

[Run] 202

| Standard | Pulse | Pre-Equilubrium | AUC Window | Drug $t_{1/2}$ | ERT | Save |

☑ Pulse 1 Active?   Copy Standard Parameters
Pulse 1 System Parameters:
64 — $S_1$ = [0.04] (amount/hrs)
66 — $k_{d1}$ = [0.03465] (1/hrs) Half life: [20] (hrs)
68 — $k_{T12}$ = [0.0693] (1/hrs) Half life: [10] (hrs)
70 — $k_{d2}$ = [0.009625] (1/hrs) Half life: [72] (hrs)
Pulse 1 Time Parameters:
Common Pulse Settings: ⊟ (click to hide)

```
Custom (enter values below)
Twice a day
Once a day
Once every other day
Once a day 1 on 6 off
Once a day 2 on 5 off
Once a day 3 on 4 off      -112
Once a day 4 on 3 off
Once a day 7 on 7 off
Once a day 14 on 14 off
Run All Consecutively
```

74 — $t_{plstart}$ = [0] (hrs) ⎫
76 — $t_{pldur}$ = [20] (hrs) ⎬ 72
78 — $t_{plint}$ = [24] (hrs) ⎪
80 — $n_{pl}$ = [3] (hrs) ⎭

☑ Repeat Pulse 1 [2] times, every [168] (hrs)
☑ Graph Pulse 1? _-__-__-__-

FIG. 15B 211
                                                          212            ↙
| Run |
| Standard | Pulse | Pre-Equilubrium | AUC Window | Drug $t_{1/2}$ | ERT | Save |

Intergrated Weighted Enzyme Activity
☑ Active?
Substrate concentration:

150 — $C_{Substrate}$ = [10] *$K_m$ (0.1 to 1000)

☐ Optional $C_{Substrate}(s)$ [1] , [100]

Max drug concentration:

152 — $C_{max}$ = [50] *$K_i$ (0 to 1000)

☐ Constant for [4] (hrs) at $C_{max}$

Concentration Curve Shape: ⊙ Exponential ○ Sine2

---
Drug elimination rate constant:
154 — $k_{drug}$ = [0.17325] (1/hrs) Half life: [4] (hrs)
Time to max drug level:
156 — $t_{rise}$ = [3 ▽] (hrs) rise to $C_{max}$
---

☐ *Control pulse on/off at [1] *$K_i$?

* If checked, $K_i$ on/off overrides current Pulse 1 time parameters from the Pulse tab.

Graph Options:
☑ Graph Drug Concentration $C_d(t)$? _____
☐ Graph Single Pulse $C_d(t)$? _____
☐ Graph V factor? _____
☑ Graph Weighted N2(t)? _____
☑ Graph Weighted N2(t)$_{no\ drug}$ − − − − −

MULTIPLE COMPARTMENT DOSING MODEL

CROSS-REFERENCE TO RELATED APPLICATION

This application claims the benefit of U.S. Provisional Patent Application No. 61/108,192 filed on Oct. 24, 2008, the contents of which are incorporated by reference herein.

FIELD OF THE INVENTION

The disclosure generally relates to the modeling of a dosing regimen for drugs. More particularly, the disclosure is directed to the modeling of a dosing regimen for drugs that bind to target proteins found in multiple compartments within cells or outside of cells and that can be transferred between different compartments, and where the binding of the drug to the target protein can affect the properties of the protein within each compartment and the rate at which the protein is degraded and transferred between different compartments.

BACKGROUND OF THE INVENTION

Methods for modeling dosing regimens and the distribution of drugs as a function of time in the body exist and are widely used to aid in the process of optimization of dosing, meaning maximizing drug exposure and efficacy while minimizing safety risks to a patient. FIG. 1 (1) provides a typical two compartment model, often used to simulate the distribution of a drug between two compartments 2, 3 over time, such as the circulation and the GI tract, given the input dose 4 and various transfer rate constants ($k_{12}$ (5), $k_{21}$ (6), $k_{10}$ (7)). In a typical model, a bolus dose of the drug enters the system 4 and the distribution with time is governed by the various transfer rates ($k_{12}$ (5), $k_{21}$ (6), $k_{10}$ (7)). In these models, the rate constants that describe the movement of material between compartments remain constant over time with the transfer rates proportional to the relevant rate constant multiplied by the concentration in a given compartment, and the model predicts how the drug distributes throughout the system as a function of time. Although the two compartment model of FIG. 1 may be used to model the distribution of an administered drug, it is not appropriate for modeling the flow of a target protein, rather than the drug, between two different cellular or extra-cellular compartments under the influence of an administered drug, for several reasons.

First, the transfer rate constants for the protein upon binding to the drug may not remain constant. When a drug, such as a Pharmacological Chaperone, enters the cell its purpose is to bind to the target protein and change the physical properties of the protein, which is expected to change the rate at which the protein is degraded and the rate at which the protein exits the initial binding compartment. Other properties of the protein may also change in the presence of the drug, such as the ability to carry out some reaction. If the target protein is an enzyme, the presence of the drug may affect the ability of the enzyme to catalyze the turnover of particular biological substrates. In order to effectively simulate the effect of the drug on the target protein and its location and activity, a model is needed. The model must be able to handle transfer and degradation rate constants that may change upon binding to the drug, and the model must be capable of simulating the effects of the drug on the system as the drug concentration changes with time.

Second, degradation of the protein can occur from either compartment, not only from the first compartment as in the standard drug distribution model. Third, the activity of the protein in biocompartment two must be captured. The model must be able to calculate the activity of the protein in biocompartment two, as a function of time, in the presence of a certain amount of a substrate and a certain amount of a drug.

The key differences discussed above motivated the creation of a new model that is appropriate for a new type of drug mechanism, and that can simulate the movement and activity of the target protein rather than the drug itself. In addition, software and methods were created to handle various types of user input and to calculate and visualize the computed results. Thus, it is advantageous to provide a new software application that can be used to perform "computational experiments", test hypotheses, design and test dosing regimens, predict possible outcomes, and to generally provide insight and information relevant to the complex but important process of evaluating and optimizing dosing regimens for drugs that affect the stability, transport, and net activity of the target proteins.

SUMMARY OF THE INVENTION

The present invention includes a method, a system, a computer-implemented method, and a computer-readable medium for the modeling of a dosing regimen for drugs that bind to target proteins.

According to aspects illustrated herein, there is provided a method for modeling a dosing regimen for a medicament. The method includes providing a system having at least two biocompartments selected from the group consisting of intracellular and extracellular regions. The method determines steady state levels in each of the at least two biocompartments by assigning variables to represent a protein production rate in one of the at least two biocompartments, a degradation rate constant for each of the at least two biocompartments, and a transport rate constant between the at least two biocompartments using a set of equations. After that, the method provides for modifying values of the assigned variables in the set of equations to use the set of equations to calculate an amount of at least one protein in one of the at least two biocompartments to which the at least one protein is being transported. The equations reflect selected characteristics of the at least one protein and one or more drug pulse parameters, the one or more drug pulse parameters include a start time, a duration, an interval time, a number of pulses, an amount of drug, and a number of times the settings are repeated. Next, the method calculates a weighted value of proteins in one or more of the at least two biocompartments to which the at least one protein is being transported, as a function of time, by multiplying an amount of at least one protein in the one of the at least two biocompartments to which the at least one protein is being transported by a calculated factor. The calculated factor is determined using a drug concentration pulse curve and a set of input parameters including a substrate concentration, a maximum drug concentration, a rise time, and a drug elimination half-life. The weighted value over a time period is then integrated to find a weighted area under the curve. Then, the method calculates a non-drug value of the at least one protein in the one of the at least two biocompartments to which the at least one protein is being transported. The non-drug value is an amount of the at least one protein in the one of the at least two biocompartments to which the at least one protein is being transported without the addition of a drug. The non-drug value is also integrated over the time period to find a non-drug area under the curve. Finally, the method evaluates one or more dosing regimens by comparing the weighted area under the curve and the non-drug area under the curve of the at least one protein in the one of the at least two biocompartments to which the at least one protein is being transported over the time period to determine a net effect of the drug over the time period.

According to further aspects illustrated herein, there is provided a system for modeling a dosing regimen of a medicament. The system includes a display device, a data store comprising a plurality of values for modeling a dosing regime of a medicament, and a service delivery device operatively connected to the display device and the data store. The service delivery device includes a processor and a memory for storing instructions that, in response to receiving a request to model the dosing regimen of a medicament, causes the processor to provide a system including at least two biocompartments selected from the group consisting of intracellular and extracellular regions. The processor then determines steady state levels in each of the at least two biocompartments by assigning variables to represent a protein production rate in one of the at least two biocompartments, a degradation rate constant for each of the at least two biocompartments, and a transport rate constant between the at least two biocompartments using a set of equations. The processor provides for modifying values of the assigned variables in the set of equations to use the set of equations to calculate an amount of at least one protein in one of the at least two biocompartments to which the at least one protein is being transported, as a function of time, the equations reflect selected characteristics of the at least one protein and one or more drug pulse parameters. The one or more drug pulse parameters include a start time, a duration, an interval time, a number of pulses, an amount of drug, and a number of times the settings are repeated. The processor then calculates a weighted value of the at least one protein in one of the at least two biocompartments to which the at least one protein is being transported by multiplying the amount of the at least one protein in one of the at least two biocompartments to which the at least one protein is being transported, the factor being determined using a drug concentration pulse curve and input parameters including a substrate concentration, a maximum drug concentration, a rise time, and a drug elimination half-life. The processor integrates the weighted value over a time period to find a weighted area under the curve. Then, the processor calculates a non-drug value of the at least one protein in the one of the at least two biocompartments to which the at least one protein is being transported. The non-drug value is an amount of the at least one protein in the one of the at least two biocompartments to which the at least one protein is being transported without the addition of a drug. The non-drug value is also integrated over the time period to find a non-drug area under the curve. Finally, the processor evaluates one or more dosing regimens by comparing the weighted area under the curve and the non-drug area under the curve of the at least one protein in the one of the at least two biocompartments to which the at least one protein is being transported over the time period to determine a net effect of the drug over the time period.

According to further aspects illustrated herein, there is provided a computer-implemented method for modeling a dosing regimen. The computer-implemented method includes providing a system having at least two biocompartments selected from the group consisting of intracellular and extracellular regions. The computer-implemented method determines steady state levels in each of the at least two biocompartments by assigning variables to represent a protein production rate in one of the at least two biocompartments, a degradation rate constant for each of the at least two biocompartments, and a transport rate constant between the at least two biocompartments using a set of equations. After that, the computer-implemented method provides for modifying values of the assigned variables in the set of equations to use the set of equations to calculate an amount of at least one protein in one of the at least two biocompartments to which the at least one protein is being transported. The equations reflect selected characteristics of the at least one protein and one or more drug pulse parameters. The one or more drug pulse parameters include a start time, a duration, an interval time, a number of pulses, an amount of drug, and a number of times the settings are repeated. Next, the computer-implemented method calculates a weighted value of proteins in one or more of the at least two biocompartments to which the at least one protein is being transported, as a function of time, by multiplying an amount of at least one protein in the one of the at least two biocompartments to which the at least one protein is being transported. The calculated factor is determined using a drug concentration pulse curve and a set of input parameters including a substrate concentration, a maximum drug concentration, a rise time, and a drug elimination half-life. The weighted value over a time period is then integrated to find a weighted area under the curve. Then, the computer-implemented method calculates a non-drug value of the at least one protein in the one of the at least two biocompartments to which the at least one protein is being transported. The non-drug value is an amount of the at least one protein in the one of the at least two biocompartments to which the at least one protein is being transported without the addition of a drug. The non-drug value is also integrated over the time period to find a non-drug area under the curve. Finally, the computer-implemented method evaluates one or more dosing regimens by comparing the weighted area under the curve and the non-drug area under the curve of the at least one protein in the one of the at least two biocompartments to which the at least one protein is being transported over the time period to determine a net effect of the drug over the time period.

According to further aspects illustrated herein, there is provided a computer-readable medium for modeling a dosing regimen for a medicament. The computer-readable medium includes instructions executable on a computing device that, when applied to the computing device causes the device to provide a system including at least two biocompartments selected from the group consisting of intracellular and extracellular regions. Then, the system uses a method to determine steady state levels in each of the at least two biocompartments by assigning variables to represent a protein production rate in one of the at least two biocompartments, a degradation rate constant for each of the at least two biocompartments, and a transport rate constant between the at least two biocompartments using a set of equations. The method provides for modifying values of the assigned variables in the set of equations to use the set of equations to calculate an amount of at least one protein in one of the at least two biocompartments to which the at least one protein is being transported. The equations reflect selected characteristics of the at least one protein and one or more drug pulse parameters. The one or more drug pulse parameters include a start time, a duration, an interval time, a number of pulses, an amount of drug, and a number of times the settings are repeated. The method calculates a weighted value of the at least one protein in the one of the at least two biocompartments to which the at least one protein is being transported, as a function of time, by multiplying the amount of the at least one protein in the one of the at least two biocompartments to which the at least one protein is being transported. The calculated factor being determined using a drug concentration pulse curve and input parameters including a substrate concentration, a maximum drug concentration, a rise time, and a drug elimination half-life. The weighted value over a time period is then integrated to find a weighted area under the curve. Then, the method calculates a non-drug value of the at least one protein in the one of the at least two biocompartments to which the at least one protein is being transported. The non-drug value is an amount of the at least one protein in the one of the at least two biocompartments to which the at least one protein is being transported without the addition of a drug. The non-drug value is also integrated over the time period to find a non-drug area under the curve. Finally, the method evaluates one or more dosing regimens by comparing the weighted area under the curve and the non-drug area under the curve of the at least one protein in the one of the at least two biocompartments to which the at least one protein is being transported over the time period to determine a net effect of the drug over the time period.

Other objects and features of the present invention will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

FIG. 5 provides a computer screen shot of a list of definitions of variables for use with a set of input parameters and the dosing model of the present invention.

FIGS. 7A-C provide computer screen shots of the present invention with a set of input parameters and a graphical depiction of the variables for drug pulses added to the dosing model.

FIGS. 8A-D provide computer screen shots of a drug dosing model of the present invention with a set of input parameters and a graphical depiction of the enzyme amounts over a period of time.

FIG. 9 provides a computer screen shot of a graphical depiction of an exponential drug concentration pulse curve.

FIGS. 12A-C provide computer screen shots of a drug dosing model of the present invention with a set of input parameters and a graphical depiction of the weighted and non-weighted enzyme amounts over a period of time.

Figure 13:
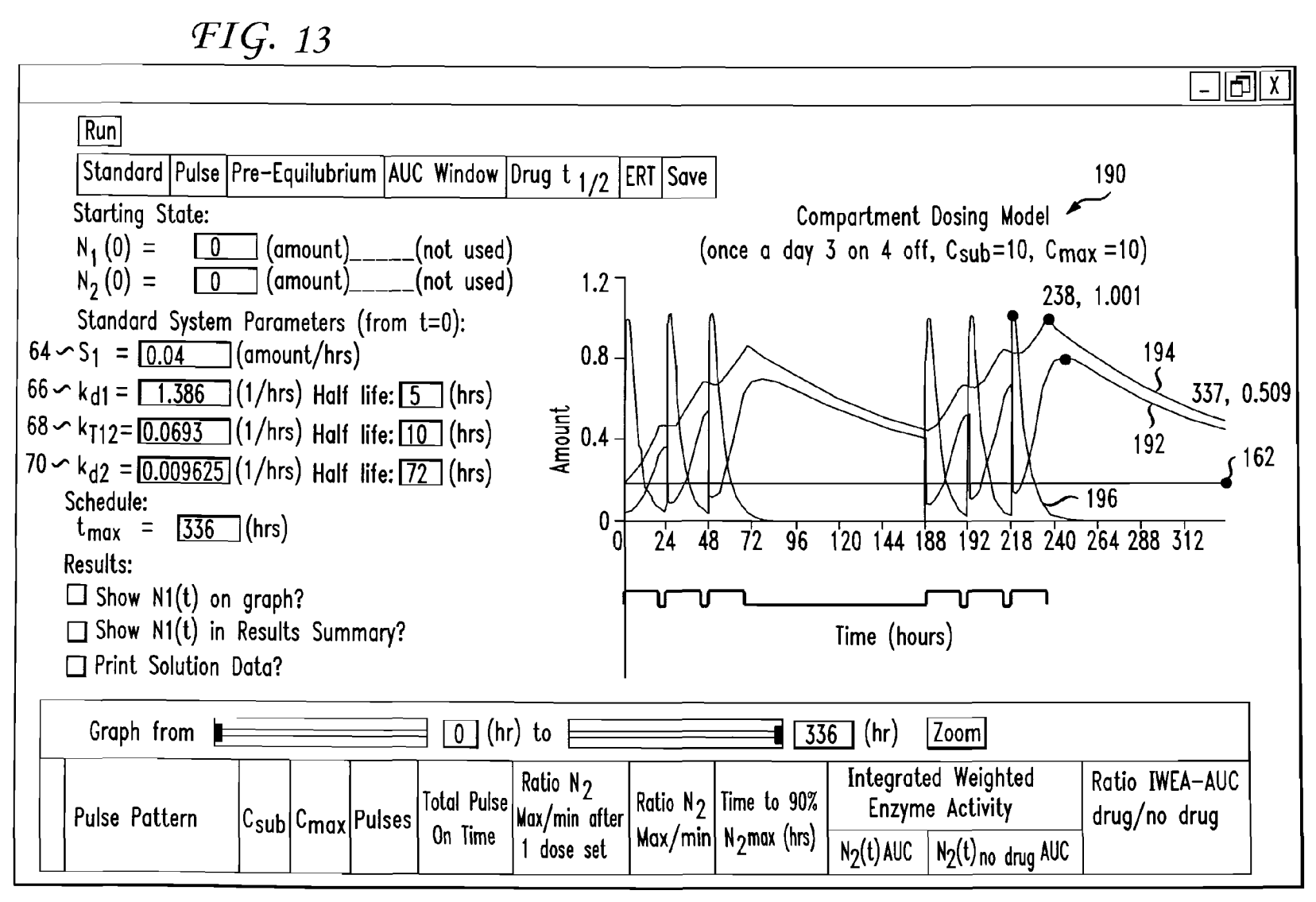

FIGS. 13, 14A-C, and 15A-C provide computer screen shots of a drug dosing model of the present invention with a set of input parameters and a graphical depiction of enzyme amounts over a period of time.

Like reference symbols in the various drawings indicate like elements.

DETAILED DESCRIPTION OF THE PREFERRED EMBODIMENTS

Figure 1:
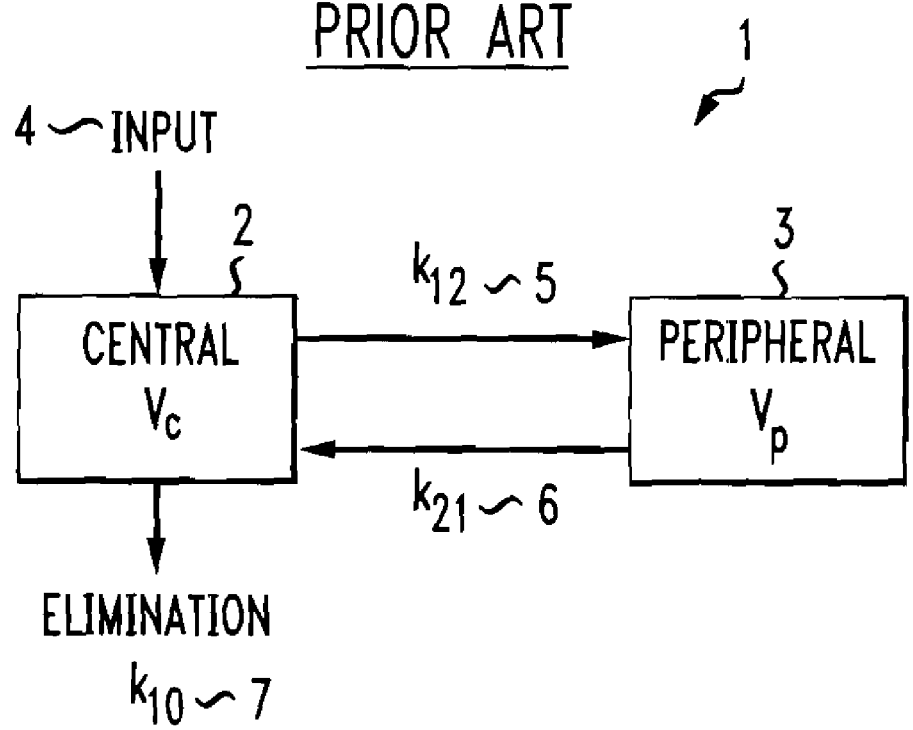
FIG. 1 illustrates a typical two compartment dosing model for distribution of a drug between two compartments over time.

The invention disclosed herein provides for the modeling of drug dosing regimens for drugs that bind to target proteins as used in biological systems having at least two biocompartments. More specifically, the invention provides an exploratory tool to assist in optimizing the dosing to maximize drug efficacy with minimization of risk to a patient.

The term "drug" includes pharmaceutically active medicaments and other biological affecting agents for use in the treatment and/or prevention of a disease in mammals and particularly for humans.

The terms "biocompartments" or "compartments" include sub-cellular regions or organelles within cells, whole cells, and extracellular regions of the body.

The term "protein" is meant to be used in its common definition and includes a macromolecule composed of one or more linear polypeptide chains which is folded into a characteristic three-dimensional shape or conformation in its native, biologically active state. The categories of proteins include enzymes. Thus, the non-limiting examples provided herein may refer to enzymes for illustrative purposes only, and the use of other proteins are fully contemplated within the scope of this invention.

The term "weighting factor" refers to the multiplication of the amount of protein in one of the compartments by a calculated factor that depends on the concentration of the drug and the concentration of the substrate. The activity weighting factor is calculated using a drug concentration curve defined by the input parameters including a maximum drug concentration, a rise time, a drug elimination rate constant, and a fixed substrate concentration.

Examples of diseases which could be amenable to chaperone therapy include Fabry Disease with the target enzyme alpha galactosidase A and the corresponding substrate globotriaosylceramide (a.k.a., Gb3, GL-3, or ceramide trihexoside); Gaucher Disease with the target enzyme glucocerebrosidase and the corresponding substrate glucocerebroside (a.k.a., glucosylceramide); and Pompe Disease with the target enzyme acid maltase and the corresponding substrate glycogen. Moreover, many more lysosome storage diseases and non-lysosomal storage diseases may also be amenable to chaperone therapy. Examples of lysosomal storage diseases include: Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Farber disease, Fucosidosis, Galactosialidosis, GM1 gangliosidosis, I-Cell disease/Mucolipidosis II, Infantile Free Sialic Acid Storage Disease/ISSD, Juvenile Hexosaminidase A Deficiency, Krabbe disease, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Salla disease, Tay-Sachs, Wolman disease. Examples of non-lysosomal storage diseases include: Alzheimer's disease, Huntington's disease, prion diseases, ALS, and Lafora disease. See also U.S. Provisional Patent Application Ser. No. 61/028,123, entitled "Treatment of Gaucher Disease with Specific Pharmacological Chaperones and Monitoring Treatment Using Surrogate Markers" filed Feb. 12, 2008; U.S. Provisional Patent Application Ser. No. 61/028,141, entitled "Method to Predict Response to Pharmacological Chaperone Treatment of Diseases" filed Feb. 12, 2008; U.S. Provisional Patent Application Ser. No. 61/035,684, entitled "Method to Predict Response to Pharmacological Chaperone Treatment of Diseases" filed Mar. 11, 2008; U.S. Provisional Patent Application Ser. No. 61/035,866, entitled "Assaying for Diagnosing and Evaluating Treatment Options for Pompe Disease" filed Mar. 12, 2008; U.S. Provisional Patent Application Ser. No. 61/035,869, entitled "Treatment of Pompe Disease with Specific Pharmacological Chaperones and Monitoring Treatment Using Surrogate Markers" filed Mar. 12, 2008; U.S. patent application Ser. No. 11/440,473 entitled "A Method for the Treatment of Pompe Disease Using 1-Deoxynjirimycin and Derivatives" filed May 17, 2006; U.S. patent application Ser. No. 11/449,528, entitled "Treatment of CNS Disorders Associated with Mutations in Genes Encoding Lysosomal Enzymes" filed Jun. 8, 2006; U.S. patent application Ser. No. 11/607,286 entitled "Combination Therapy for Treating Protein Deficiency Disorders" filed Dec. 1, 2006; U.S. patent application Ser. No. 11/749,512, entitled "Assays for Diagnosing and Evaluating Treatment Options for Fabry Disease" filed May 16, 2007; U.S. patent application Ser. No. 11/768,043, entitled "Method for the Treatment of Neurological Disorders by Enhancing the Activity of β-Glucocerebrosidase" filed Jun. 25, 2007; U.S. Patent Application Publication No. 2006/0153829, entitled "Stable Formulations of Purified Proteins" published on Jul. 13, 2006; U.S. Pat. No. 6,274,597, entitled "Method of Enhancing Lysosomal α-Galactosidase A issued Aug. 14, 2001; U.S. Pat. No. 6,583,158, entitled "Method for Enhancing Mutant Enzyme Activities in Lysosomal Storage Disorders" issued Jun. 24, 2003; U.S. Pat. No. 6,589,964, entitled "Method for Enhancing Mutant Enzyme Activities in Lysosomal Storage Disorders" issued Jul. 8, 2003; U.S. Pat. No. 6,599,919, entitled "Method for Enhancing Mutant Enzyme Activities in Lysosomal Storage Disorders" issued Jul. 29, 2003; U.S. Pat. No. 6,774,135, entitled "Method of Enhancing Lysosomal a-Galactosidase A" issued Aug. 10, 2004; U.S. Pat. No. 6,916,829, entitled "Method for Enhancing Mutant Enzyme Activity in Gaucher Disease" issued Jul. 12, 2005; U.S. Pat. No. 7,141,582, entitled "Method for Enhancing Mutant Enzyme Activities in Gaucher Disease" issued Nov. 28, 2006; PCT/US08/58668, entitled "Method for the Treatment of Fabry Disease Using Pharmacological Chaperones" filed Mar. 28, 2008; and PCT/US08/61764, entitled "Dosing Regimens for the Treatment of Lysosomal Storage Diseases Using Pharmacological Chaperones" filed Apr. 28, 2008, the entire contents all the above mentioned patents and applications are expressly incorporated herein by reference for all purposes.

Figure 2:
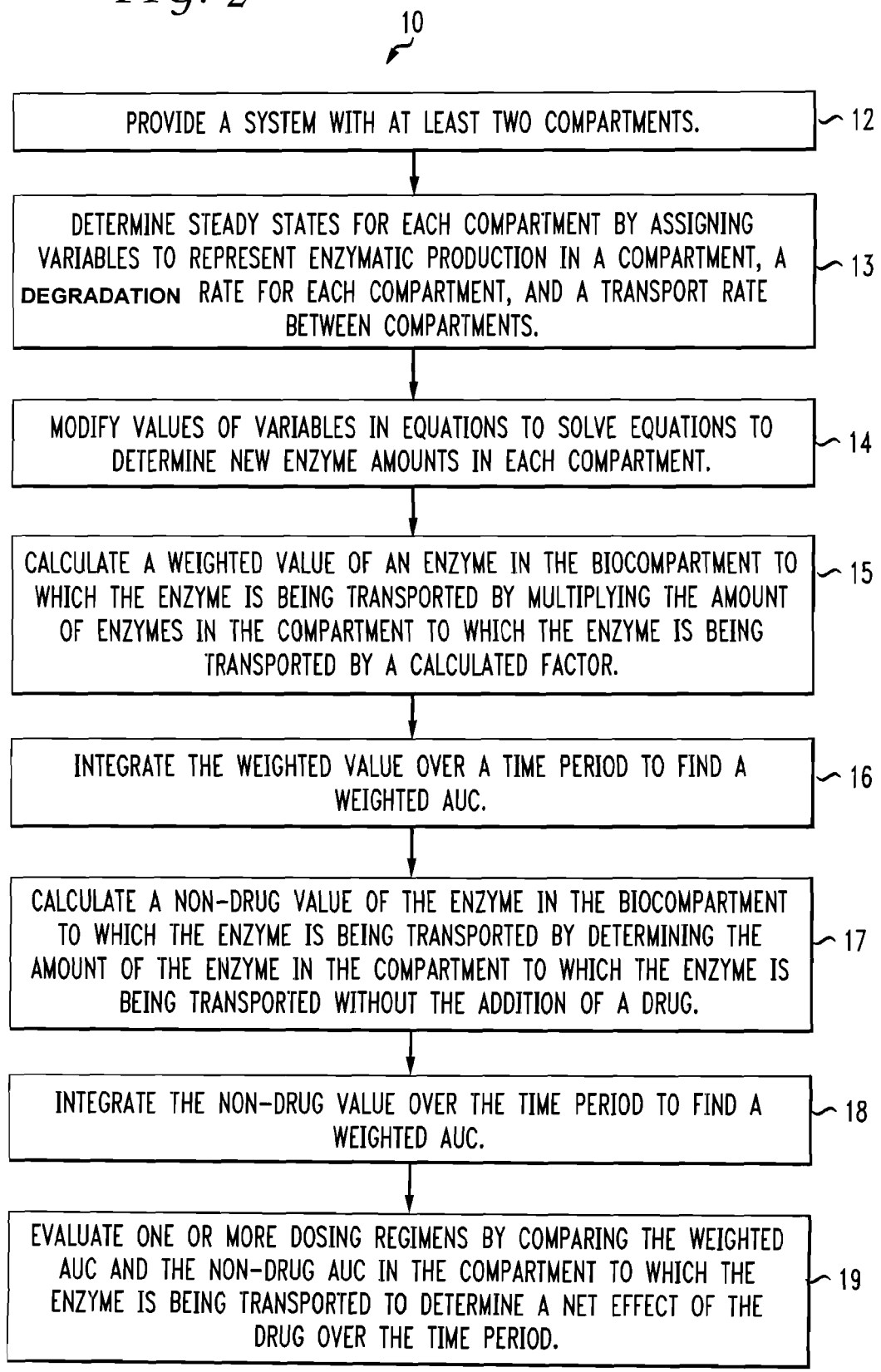
FIG. 2 illustrates an exemplary method of modeling dosing of drugs that bind to target proteins of the present invention.

FIG. 2 describes an exemplary method 10 for modeling a drug dosing regimen for drugs that bind to target proteins. The method 10, in step 12 requires providing a system with at least two biocompartments. In step 13, steady states for each biocompartment may be determined by assigning variables to represent enzymatic productions in one of the at least two biocompartments, a degradation rate constant for each biocompartment, and a transport rate constant between biocompartments using modeling equations. The values of the assigned variables in the set of equations may be modified in step 14 to determine the enzyme amounts in the biocompartment to which the enzymes are being transported to, as a function of time. The equations reflect selected characteristics of the at least one enzyme and one or more drug pulse parameters. The one or more drug pulse parameters include a start time, a duration, an interval time, a number of pulses, an amount of drug, and a number of times the settings are repeated.

Next, in step 15, a weighted value of the enzyme in the biocompartment to which the enzyme is being transported is calculated. The weighted value is the result of multiplying a calculated factor by an amount of the enzyme. The calculated factor is determined using a drug concentration pulse curve and a set of input parameters includes a substrate concentration, a maximum drug concentration, a rise time, and a drug elimination half-life. In step 16, the weighted value over a time period is integrated to find a weighted area under the curve (AUC). After that, in step 17, a non-drug value is calculated for the enzyme in the biocompartment to which the enzyme is being transported. The non-drug value is the amount of the enzyme without the addition of a drug. In step 18, the non-drug value over the time period is integrated to find a non-drug area under the curve.

Then, in step 19 one or more dosing regimens are evaluated to determine a net effect of the drug over the time period. The dosing regimens are evaluated by comparing the weighted area under the curve and the non-drug area under the curve over a period of time for the biocompartment to which the enzyme is being transported.

Figures 10, 11:
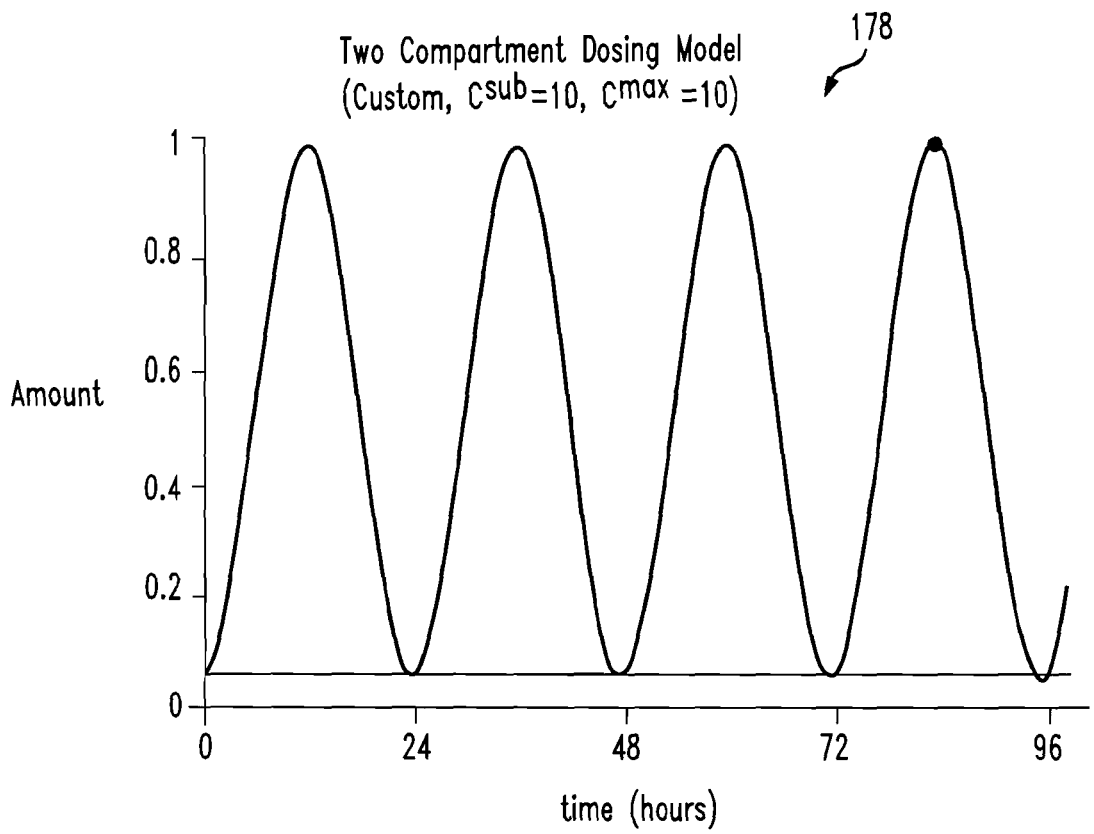
FIG. 10 provides a computer screen shot of the settings for a sinusoidal concentration curve option.
FIG. 11 provides a computer screen shot of a graphical depiction of the sinusoidal drug concentration pulse curve.

The calculated factor, from step 15, corresponds to a drug concentration curve. Examples of possible drug concentration curves include an exponential pulse curve and a sinusoidal pulse curve as illustrated in FIGS. 9 and 11 below.

Figure 3:
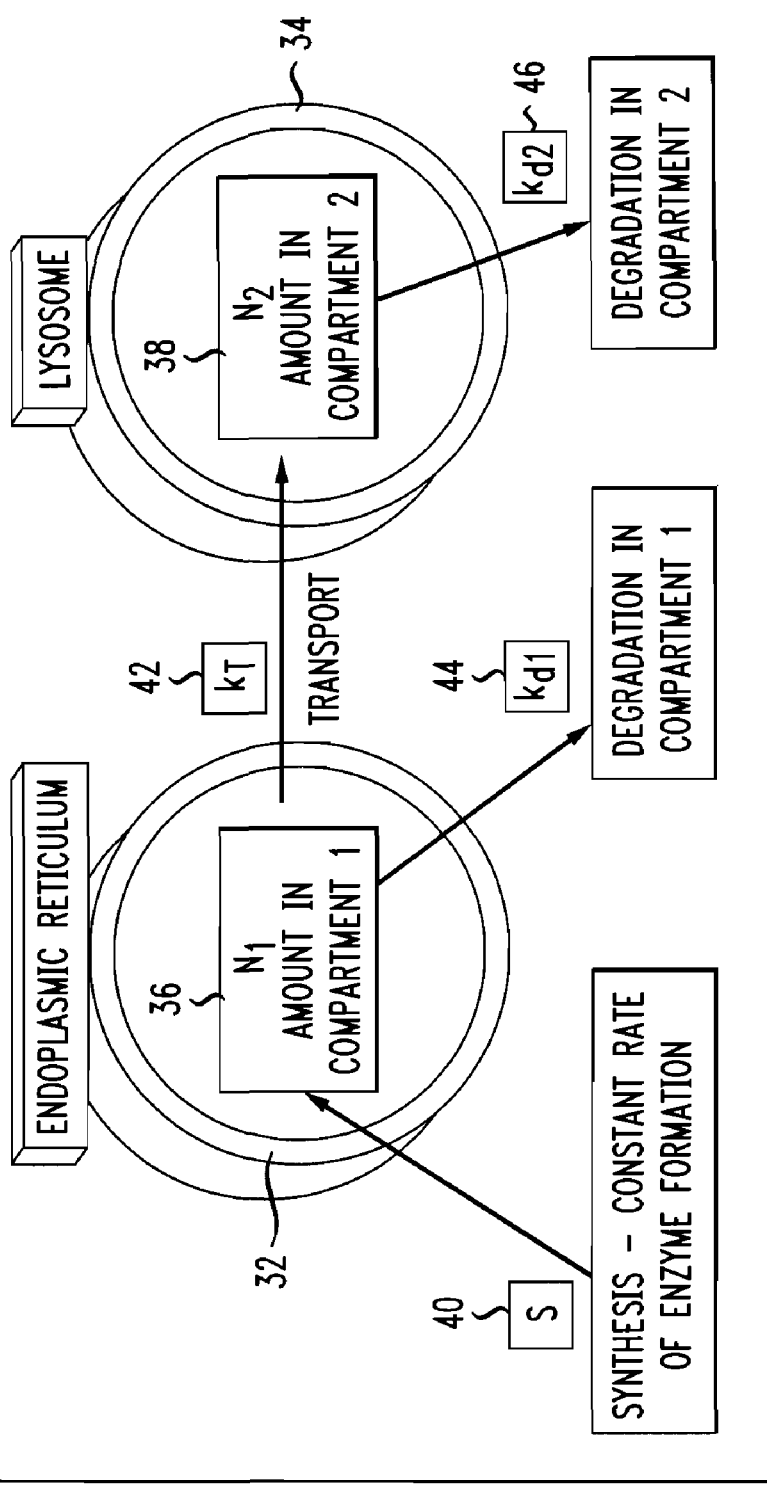
FIG. 3 is a diagram of a system for use with the method of FIG. 2.

Referring to FIG. 3, an example of a system 30 with two biocompartments, an endoplasmic reticulum 32 (biocompartment one) and a lysosome 34 (biocompartment two), is illustrated. The endoplasmic reticulum 32 is an intricate system of tubular membranes in the cytoplasm of a cell that is responsible for the synthesis and transport of materials, including enzymes 36 to and from cells. The lysosome 34 is a membrane-bound cavity in a living cell that contains enzymes 38 responsible for degrading and recycling various molecules.

Although, the system 30 uses the endoplasmic reticulum 32 and the lysosome 34 as example biocompartments, the present invention contemplates the biocompartments to include any intracellular or extracellular regions that enable synthesis of enzymes 40, the transport of materials between biocompartments 42, and/or degradation of enzymes 44, 46. Another example of a system of biocompartments includes cytoplasm and mitochondria; however, other systems contemplated may include at least two biocompartments inside a cell, at least two biocompartments outside a cell, and a combination of at least one biocompartment inside a cell and at least one biocompartment outside a cell. For example, the method for modeling a dosing regimen may be used with various proteins. Examples of proteins include interior cell membranes, exterior cell membranes, and extracellular space.

In system 30, enzymes are produced at a constant rate, or synthesis rate (S) 40 in the endoplasmic reticulum 32. The enzyme amount ($N_1$) 36 in biocompartment one 32 depends on the synthesis rate (S) 40, the transport rate constant ($k_T$) 42, and a degradation rate constant ($k_{d1}$) 44. The transport rate constant ($k_T$) 42 represents the enzymes that are transported from the endoplasmic reticulum to the lysosome. The transportation rate is ($k_T*N_1$), which is proportional to the enzyme amount ($N_1$) 36 in biocompartment one 32. Thus, enzymes that are transported from the endoplasmic reticulum to the lysosomes are defined by the transport rate constant ($k_T$) 42 with a rate of ($k_T*N_1$).

The enzymes in biocompartment one 32 are also subject to degradation rate constant ($k_{d1}$) 44, which is used to determine the degradation rate in biocompartment one 32. The degradation rate ($k_{d1}*N_1$) is proportional to the amount of enzymes ($N_1$) 36 in biocompartment one 32. Therefore, the change in the amount of enzymes ($N_1$) 36 in biocompartment one 32 over time may be described by the equation $$\frac{dN_1}{dt} = S - (k_{d1} \cdot N_1) - (k_T \cdot N_1).$$

Similarly, the amount of enzymes (N2) 38 in biocompartment two 34 depends on the transport rate ($k_T*N2$) of enzymes from the endoplasmic reticulum to the lysosome, and the degradation constant ($k_{d2}$) 46, which is proportional to the amount of enzymes in ($N_2$) 38 in biocompartment two 34. Thus, the change in the amount of enzyme ($N_2$) 38 in biocompartment two 34 over time may be described by the equation $$\frac{dN_2}{dt} = (k_T \cdot N_1) - (k_{d2} \cdot N_2).$$

To find $N_1(t)$ and $N_2(t)$, where $N_1(t)$ and $N_2(t)$ are the amounts of enzymes in $N_1$ and $N_2$, respectively, at a time, t, the above two equations may be solved explicitly as follows:

$$N_1(t) = C_1 \cdot e^{-K_1 \cdot t} + \frac{S}{K_1}$$

$$N_2(t) = C_1 \cdot \left(\frac{-k_T}{k_1 - k_{d2}}\right) \cdot e^{-K_1 \cdot t} + C_2 \cdot e^{-k_{d2} \cdot t} + \frac{S \cdot k_T}{K_1 \cdot k_{d2}}$$

$$K_1 = (k_{d1} + k_T)$$

$$C_1 = N_1(0) - \left(\frac{S}{K_1}\right)$$

$$C_2 = N_2(0) - \left(N_1(0) - \frac{S}{K_1}\right) \cdot \left(\frac{-k_T}{K_1 - k_{d2}}\right) - \left(\frac{S \cdot k_T}{K_1 \cdot k_{d2}}\right)$$

Figure 4:
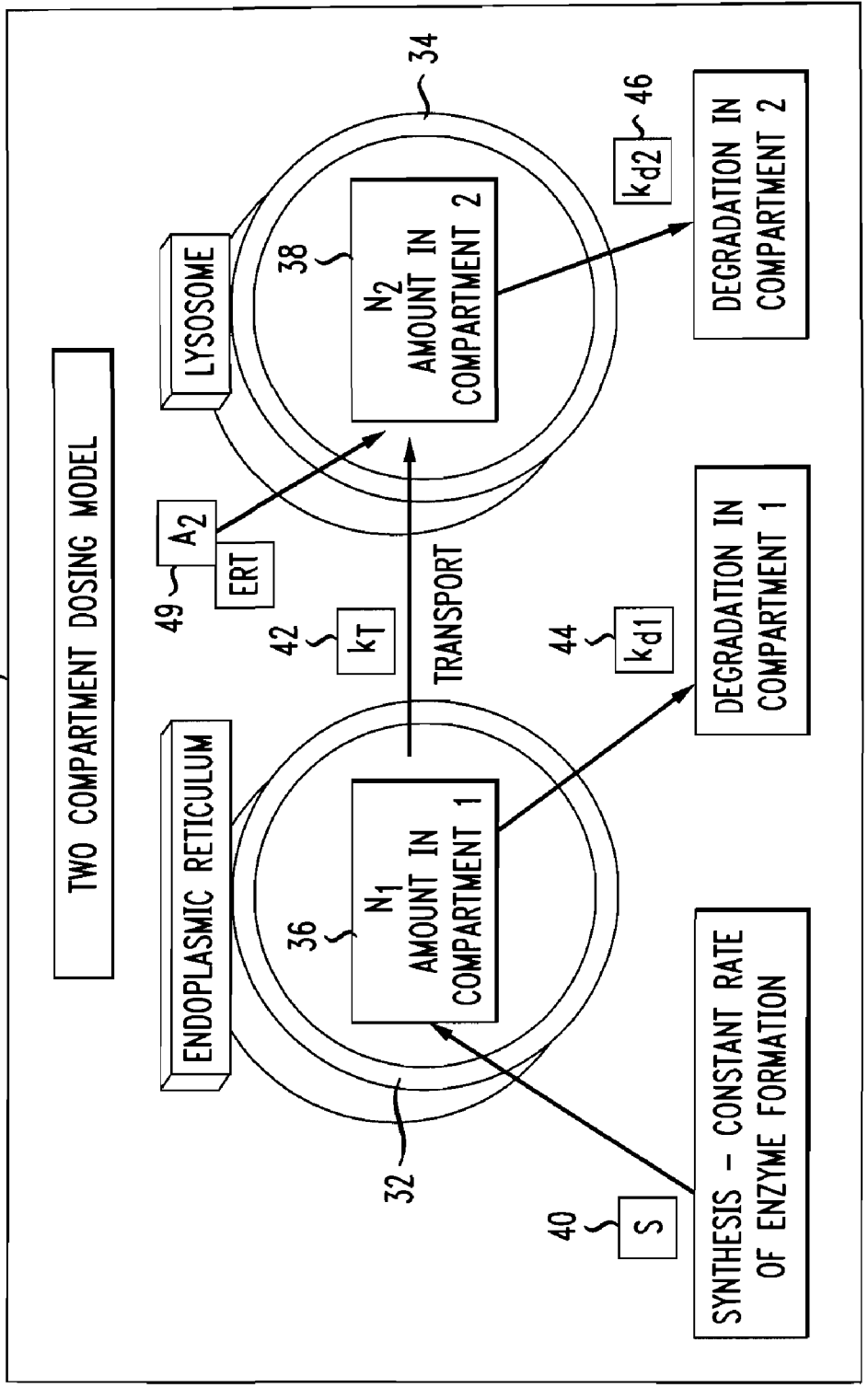
FIG. 4 is a diagram of the system of FIG. 3 with the addition of Enzyme Replacement Therapy.

FIG. 4 provides a system 48 similar to the system 30 of FIG. 3 with the addition of Enzyme Replacement Therapy (ERT). During ERT, an enzyme ($A_2$) 49 is added to biocompartment two 34 at a constant rate. The enzyme ($A_2$) 49 is being infused directly into the Lysosome. Unlike the Synthesis rate (S) 40, which is always active, the enzyme ($A_2$) 49 is turned on for brief periods, so the model handles an input pulsing type schedule. When the ERT enzyme ($A_2$) 49 is turned off ($A_2$=0), the system 48 runs the same as FIG. 3. The system 30 of FIG. 3 uses chaperone technology to increase the amount of functional enzymes that are transported from biocompartment one 32 to biocompartment two 34, and the addition of ERT, in FIG. 4, boosts the system 48 by infusing enzymes ($A_2$) 49 directly into biocompartment 2 34, which results in an increased amount of enzymes ($N_2$) 38.

Accordingly, the change in the amount of enzymes in biocompartment one ($N_1$) 36 over time may be described by the equation $$\frac{dN_1}{dt} = S - (k_{d1} \cdot N_1) - (k_T \cdot N_1).$$

However, during ERT, the change in the amount of enzyme ($N_2$) 38 in biocompartment two 34 over time may be described by the equation $$\frac{dN_2}{dt} = (k_T \cdot N_1) - (k_{d2} \cdot N_2) + A_2.$$

During ERT, the equation for the change in the amount of enzyme further includes the addition of "+$A_2$." To find $N_1(t)$ and $N_2(t)$ during ERT, where $N_1(t)$ and $N_2(t)$ are the amounts of enzymes in $N_1$ and $N_2$, respectively, at a time, t, the above two equations may be solved explicitly as follows:

$$N_1(t) = C_1 \cdot e^{-K_1 \cdot t} + \frac{S}{K_1}$$

$$N_2(t) = C_1 \cdot \left(\frac{-k_T}{k_1 - k_{d2}}\right) \cdot e^{-K_1 \cdot t} + C_2 \cdot e^{-k_{d2} \cdot t} + \frac{S \cdot k_T}{K_1 \cdot k_{d2}} + \frac{A_2}{k_{d2}}$$

$$K_1 = (k_{d1} + k_T)$$

$$C_1 = N_1(0) - \left(\frac{S}{K_1}\right)$$

$$C_2 = N_2(0) - \left(N_1(0) - \frac{S}{K_1}\right) \cdot \left(\frac{-k_T}{K_1 - k_{d2}}\right) - \left(\frac{S \cdot k_T}{K_1 \cdot k_{d2}} + \frac{A_2}{k_{d2}}\right)$$

Note, during ERT, equations for ($N_1$) 36 are the same for FIGS. 3 and 4 because the amount of enzyme ($N_1$) 36 in biocompartment one 32 remains the same. Conversely, the equations for ($N_2$) 38 are not the same during ERT because the additional enzyme ($A_2$) 49 is added. As expected, the amount of enzyme $N_2$ in biocompartment two 34 increases as the ERT rate of ($A_2$) 49 increases. However, when ERT is not being performed, the addition of enzyme ($A_2$) 49 is turned off (i.e., $A_2$=0), and the equations are identical to the original non-ERT equations, discussed above with respect to FIG. 3.

With reference to FIG. 5, a screen shot 50 of various assigned variable definitions 52 for determining the amount of enzymes in the two biocompartments 32, 34 of the system 30 is provided. The definitions of steady state level variables 54 useful in determining the steady state levels in each biocompartment include: the amount of enzymes in biocompartment one 32 at time t (56), the initial amount of enzymes 58 in biocompartment one 32 (also referred to as time 0), the amount of enzymes in biocompartment two 34 at time t (60), the initial amount of enzymes 62 in biocompartment two 34 (also referred to as time 0), the synthesis rate ($S_1$) 64 (expressed as amount/hour) in biocompartment one 32, the degradation rate constant ($k_{d1}$) 66 (expressed as 1/hour) of biocompartment one 32, the transport rate constant ($k_{T12}$) 68 (expressed as 1/hour) for biocompartment one 32 to biocompartment two 34, and the degradation rate constant ($k_{d2}$) 70 (expressed as 1/hour) in biocompartment two 34. The definitions of pulse variables 72, useful in adding pulse patterns to the dosing model, include: pulse time to start first pulse ($t_{p1start}$) 74, duration of each pulse ($t_{p1dur}$) 76, pulse interval time ($t_{p1int}$) 78, number of times pulse repeats ($n_{p1}$) 80, and ERT rate ($A_2$) 81 (expressed as amount/hour). FIG. 5, further includes the following assumptions for the above equations: (1) the degradation rates in biocompartment one 32 and biocompartment two 34 are proportional to the amounts of $N_1(t)$ (36) and $N_2(t)$ (38) at 82; and (2) the amount of enzymes ($N_1$) 36 in biocompartment one 32 is proportional to the transport rate from biocompartment one 32 to biocompartment two 34 at 82.

Figure 6:
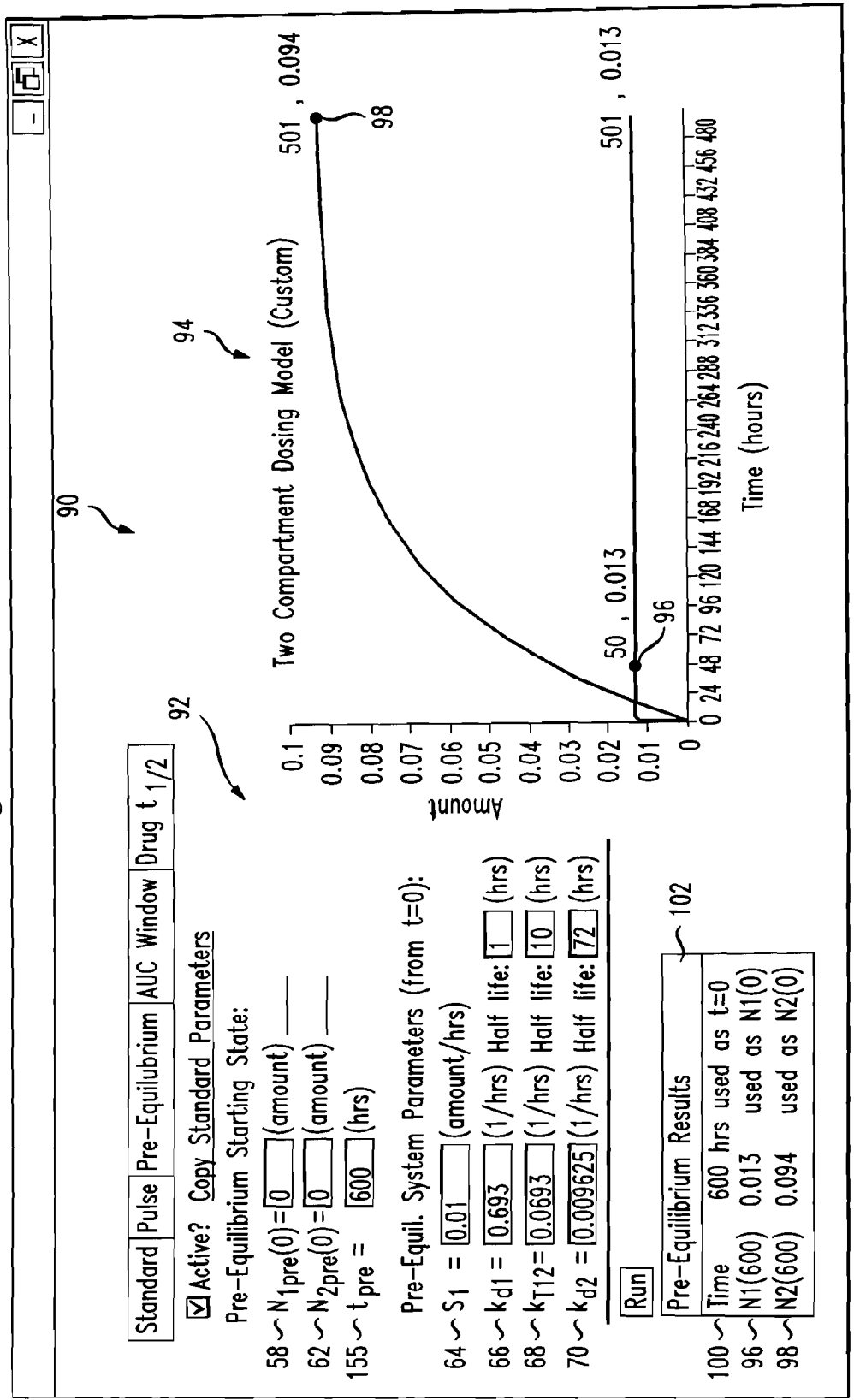
FIG. 6 provides a computer screen shot of a drug dosing model of the present invention with a set of input parameters and a graphical depiction of the steady state levels for each compartment.

FIG. 6 further provides a screen shot 90 of the variables 54 on the left side of the screen 92 and a line graph 94 on the right side of the screen graphically depicting the enzyme amounts ($N_1$) 36, ($N_2$) 38 in biocompartment one 32 and biocompartment two 34 from the initial time (t=0) through when steady state levels are reached 96, 98. Variable values are selected based on estimates of likely values in systems of interest, on specific experimental data, or are chosen to calculate the effect of certain variables on the evolution of the system and the computed output. Note the time (t) 100 was set to calculate $N_1(t)$ 36 and $N_2(t)$ 38 until t=600. Moreover, the Pre-Equilibrium Results 102 show the steady state levels of enzymes 96, 98 in biocompartment one 32 and biocompartment two 34. For the system 30 and for the values of variables $N_1(0)$ (58), $N_2(0)$ (62), $S_1$ (64), $k_{d1}$ (66), $k_{T12}$ (68), and $k_{d2}$ (70), the amount of enzyme ($N_1$) 36 is 0.013 (96) and the amount of enzyme ($N_2$) 38 is 0.094 (98).

Figure 7A:
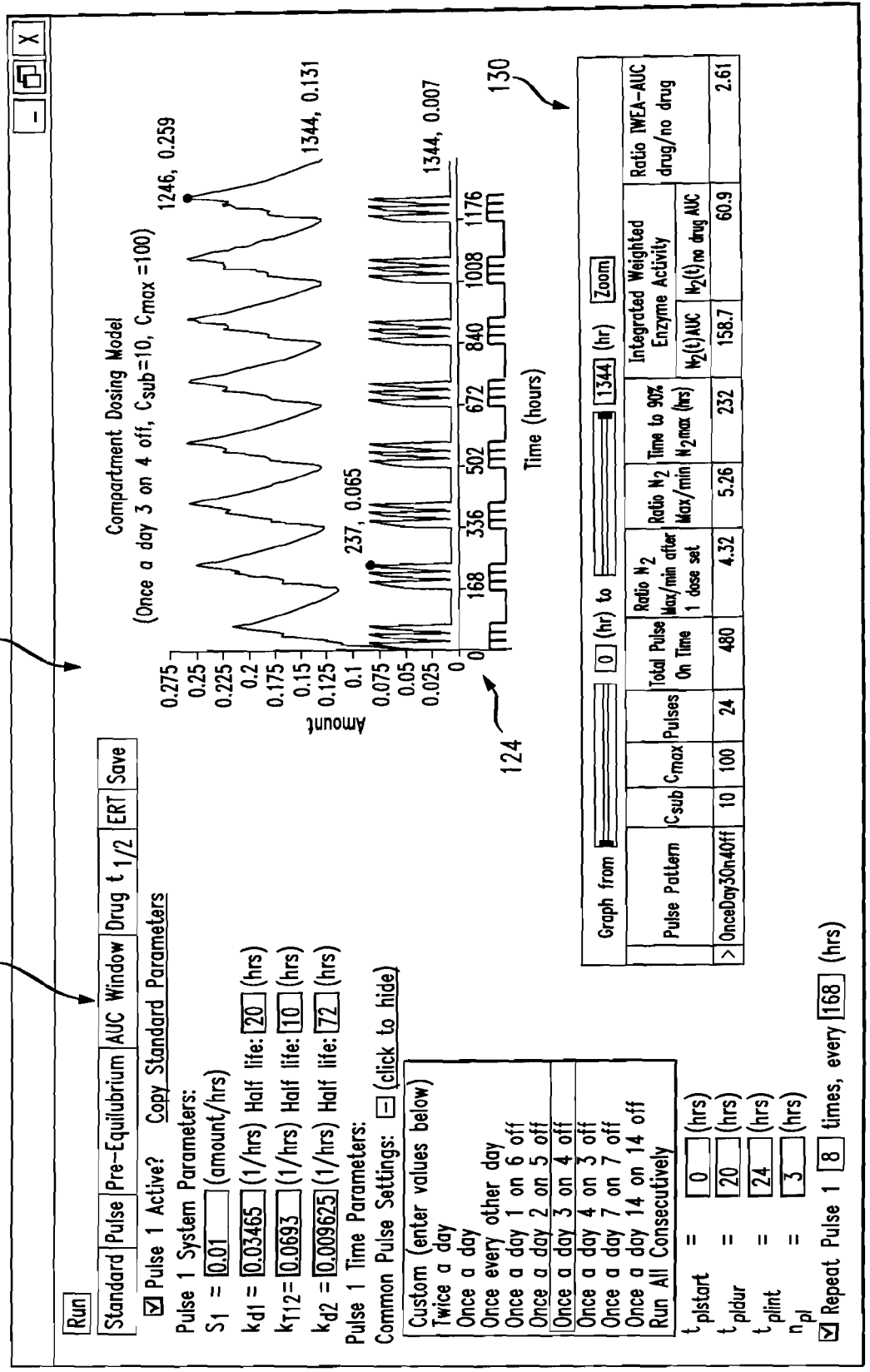

With Reference to FIGS. 7A-7C, a screen shot 110 is provided with assigned variables 111 on the left side of the screen shot 110, as shown in FIG. 7A. FIG. 7B shows the assigned variables 111 including $S_1$ (64), $k_{d1}$ (66), $k_{T12}$ (68), and $k_{d2}$ (70), which include the introduction of the drug pulse variables 72, $t_{p1start}$ (74), $t_{p1dur}$ (76), $t_{p1int}$ (78), and $n_{p1}$ (80). In addition to using the pulse variables 72, the synthesis rate ($S_1$) and rate constants, $k_{d1}$ (66), $k_{T12}$ (68), and $k_{d2}$ (70), may also be modified to characterize the pulse. The timing of the pulse may be specified by selecting a timing from the "common pulse settings" dropdown menu, a multitask listbox, or similar selection methods, such timing includes "Once a day 3 on 4 off" 112. The common pulse settings menu allow for the selection of common pulse cycles, for example, "Once a day 3 on 4 off" indicates that the drug is administered once a day for three days then there are four days of no drug being administered. If one of the common pulse settings 112 is selected, then the variables corresponding to the customizable pulse variables $t_{p1start}$ (74), $t_{p1dur}$ (76), $t_{p1int}$ (78), and $n_{p1}$ (80) will automatically be assigned to achieve the desired pulse settings.

Custom pulse settings may also be specified by assigning values to each individual variable, such as the pulse time to start first pulse $t_{p1start}$ (74), the duration of each pulse $t_{p1dur}$ (76), the pulse interval time $t_{p1int}$ (78), and the number of times the pulse repeats $n_{p1}$ (80). Whether a common pulse setting is selected or a custom pulse setting is selected a user may modify the values for any of the variables to finely adjust or customize the dosing model for an individual patient. Other options for the users include the option to set up repetitions for the pulse pattern 116, such as setting the dosing regimen to run for 8 weeks, provide variables for standard pulse parameters 118, activate an additional or second pulse (not shown), and copy pulse parameter (not shown) that enables the first pulse to be copied to the second pulse.

A further feature includes the option to have a drug concentration to take over the pulse schedule by using the drug concentration to specify the drug pulse as designated number of hours. The program then looks at the drug concentration going up and down to determine the length of each pulse using a dynamic calculation. This option may be used in place of a preset pulse that requires the user to enter the information for pulse cycles. Therefore, instead of entering pulse information, the user may tell the program to determine the pulse schedule by the drug concentration.

To calculate the amount of enzymes ($N_1$) 36 in biocompartment one 32 and the amount of enzymes ($N_2$) 38 in biocompartment two 34 while a pulse is active, the model uses the above equations for $N_1(t)$ (36) and $N_2(t)$ (38) as the intervals with no pulse. The difference is that at the start of the pulse period, $N_1(t)$ (36) and $N_2(t)$ (38) are initialized with the current values, and the pulse input parameters $S_1$ (64), $k_{d1}$ (66), $k_{T12}$ (68), and $k_{d2}$ (70) are used for the duration of the pulse. When the pulse completes, ($N_1$) 36 and ($N_2$) 38 are reinitialized and the standard parameters are put back into use until the next pulse starts.

As the variables are modified on the left side of screen shot 110, the graph 124, shown in FIGS. 7A and 7C, on the right side of screen shot 110 may be configured to show the dosing model during a designated interval, i.e., between 0 hours (120) and 1344 hours (122). The interval may be adjusted to provide the user with various zoom 114 levels and views of the graph 124. The zoom 114 feature allows a user to zoom in to view smaller portions of the graph or zoom out to view larger portions of the graph.

For example, when the graph 124 is zoomed out, as shown in FIG. 7C, a user can determine that after the third day of administering the drugs, the biocompartment two 34 reaches the peak amount of non-weighted enzymes ($N_2$) 38 at 0.085 enzymes 126; and graph 124 also shows that the biocompartment two 34 contains 0.259 enzymes 128 after reaching the peak amount of weighted enzymes ($N_2$) 38 on day eight. There is also a drug pulse result chart 130 as shown in FIG. 7C under the graph 124 to provide a summary of information about the dosing model selected.

Referring to FIGS. 8A-D, a screen shot 140 illustrates the amount of enzyme in biocompartment two 34 with weighted $N_2$ (146) and non-weighted $N_2$ (148) values to provide more realistic depictions of drug concentration. Drug pulse parameters 141 are found on the left panel of the screen shot 140, a graph 144 is shown on the upper right panel of the screen shot 140, and a chart 158 is shown on the lower right panel of the screen shot 140. The screen shot 140 provides the ability to compare dosing regimens may be compared side by side using the table 158 and/or the graph 144.

Figure 8A:
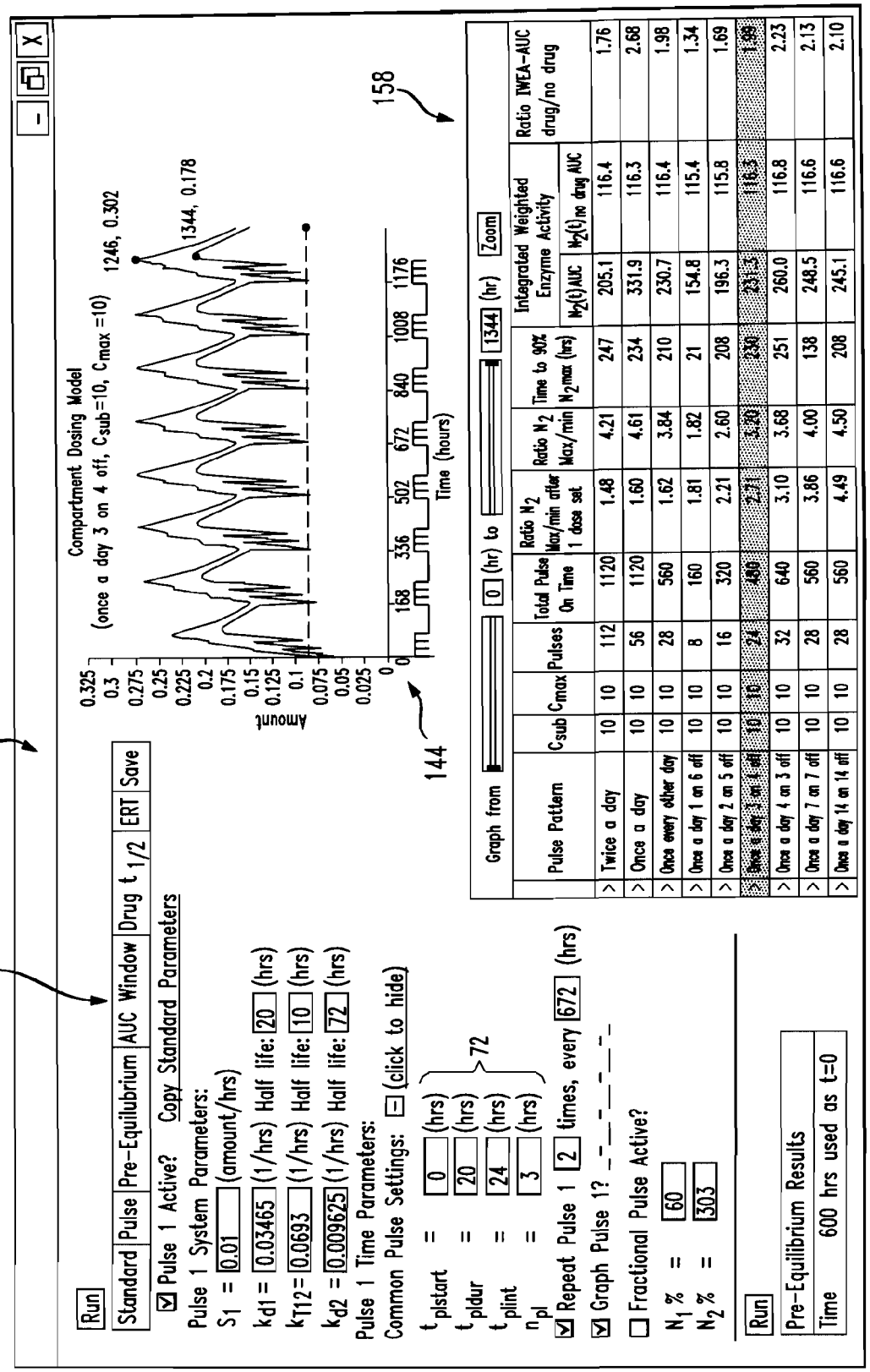
Figure 8C:
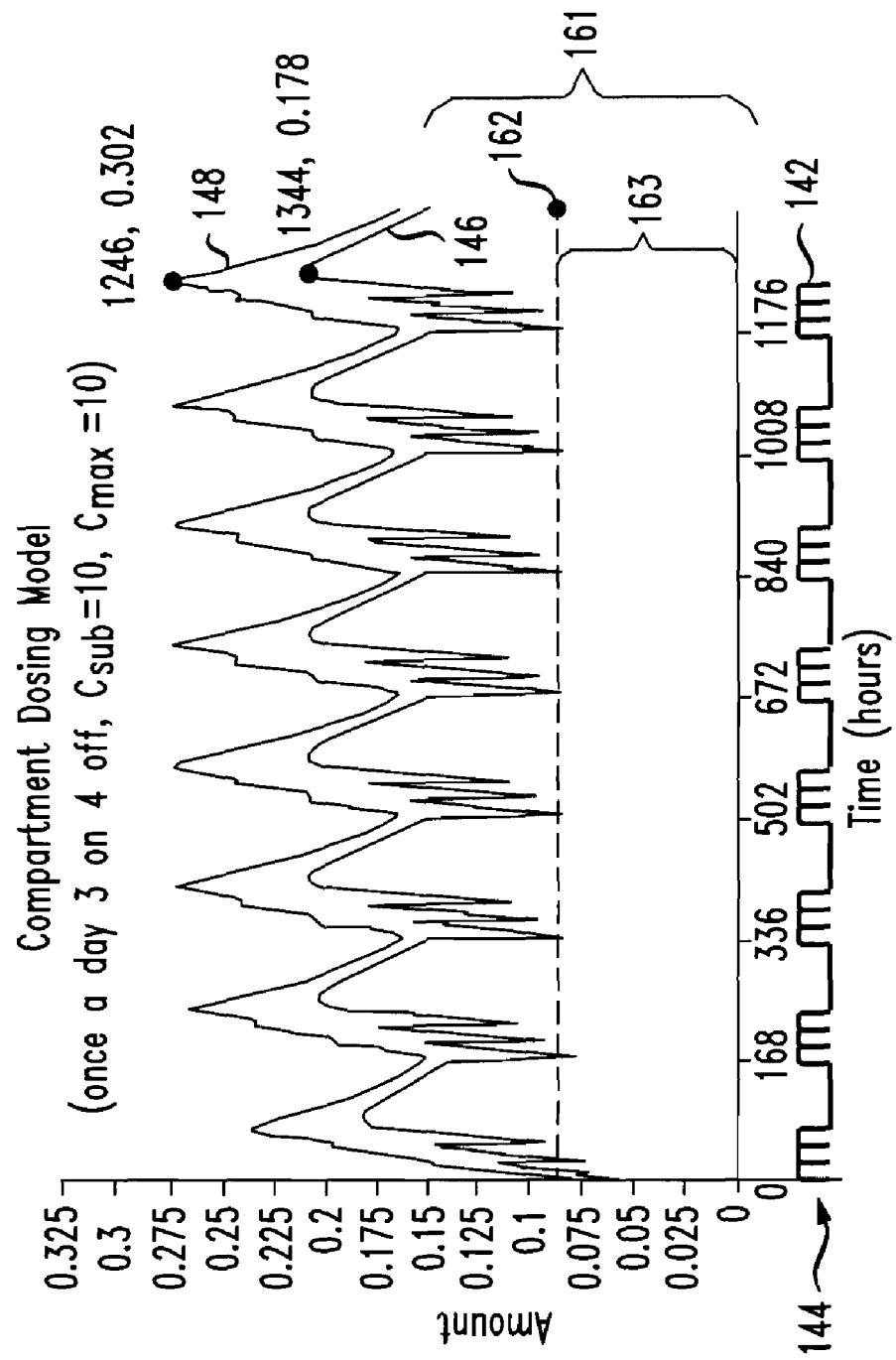

The graph 144, as illustrated in FIG. 8C, provides multiple graphical depictions of enzymes in the biocompartment two 34. Reference 142 shows the use of rectangular shaped drug pulses, rectangular shaped drug pulses only simulate an instantaneous transition from the non-pulse parameters to the pulse parameters. In the body, the concentration of the drug after it is introduced does not rise instantaneously, but may for example, rise to its peak, as shown by reference 152, within some amount of time and then decays exponentially. To simulate this more realistic pulse shape for the "Area Under the Curve" (AUC) calculation, a weighted $N_2$ (146) and non-weighted $N_2$ (148) may be calculated.

Reference 148 shows a graphical depiction of the non-weighted amounts of enzymes ($N_2$) 38 in biocompartment two 34 and reference 146 shows a graphical depiction of a weighted amount of enzymes ($N_2$) 38 in biocompartment two 34. The weighted amount of ($N_2$) 38 in biocompartment two 34 may be integrated to find the area under the curve, shown by reference 161 on the graph 144 and referenced 165 on the chart 158 in FIG. 8D under the category "Integrated Enzyme Activity" 164. In contrast, reference 162 provides a graphical depiction of the enzymes ($N_2$) 38 in biocompartment two 34 without the drug. The amount of enzyme ($N_2$) 38 in biocompartment two 34 without any drug may also be integrated to find the area under the curve, shown by reference 163 on the graph 144 and by reference 166 on the chart 158.

Figure 8D:
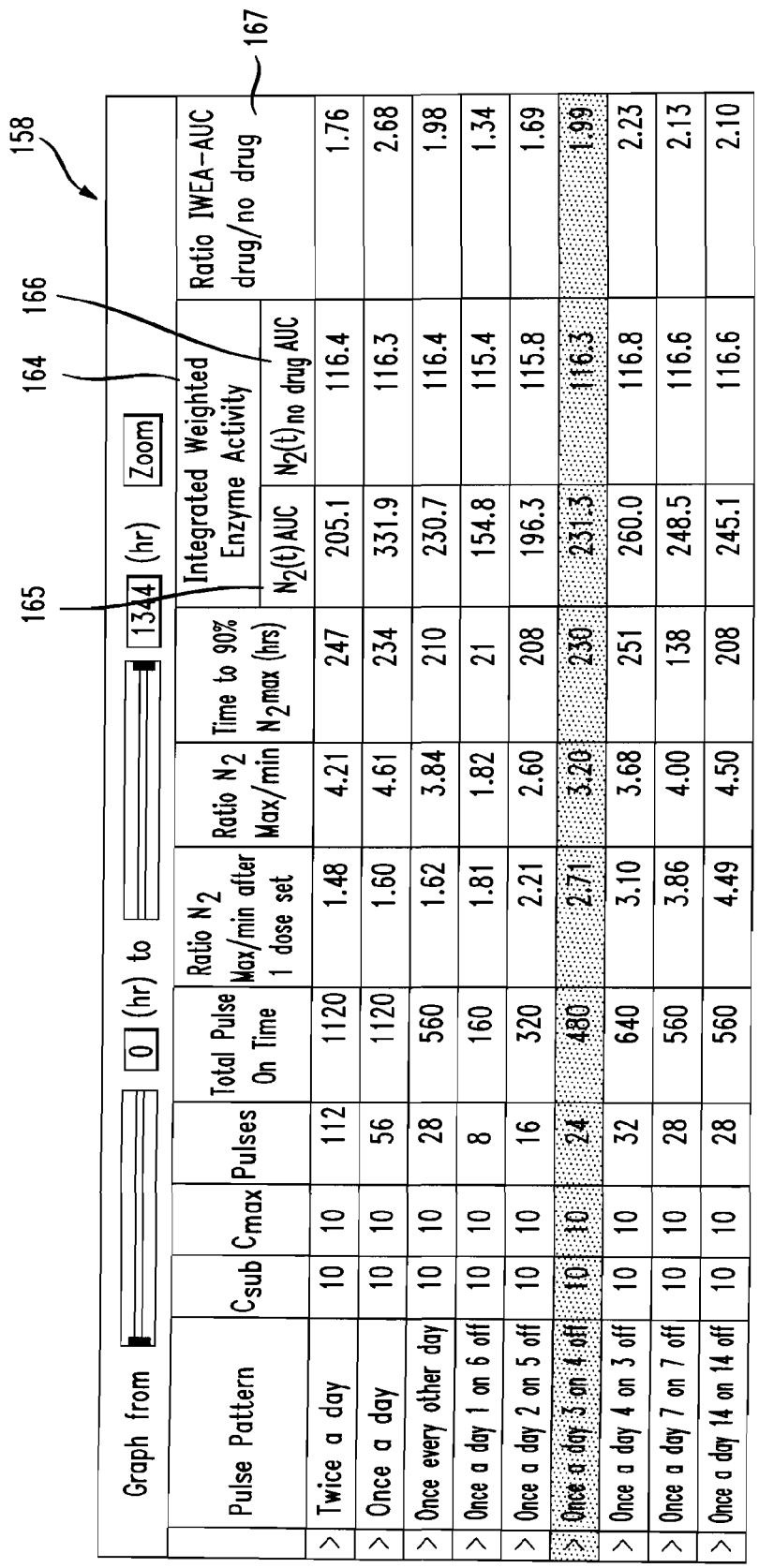

The values for the integrated weighted enzyme activity of the amount of the enzyme ($N_2$) 38 in biocompartment two 34 with and without drugs may then be calculated in order to evaluate various possible dosing regimens. One evaluation method includes determining the net effect of the drug over time by calculating a ratio, as shown in FIG. 8D by reference 167 on chart 158. The chart 158 shows the ratio 167 as the result of a comparison of the areas under the curve values for drug/no drug. Ratios 167 greater than 1.0 are considered to have increased the net amount of enzyme activity, with the higher the ratio the greater the increase in activity in the biocompartment due to the administration of the drug with the specified regimen over the time window. Thus, the higher the ratio the greater the net increase of the enzyme activity in the biocompartment, which may indicate a greater effect of the therapy.

The weighted value for (N$_2$) 38 may be calculated by multiplying the standard (N$_2$) 38 by a calculated V factor (V$_f$). The calculated V factor is based on standard textbook equations for the activity of an enzyme in the presence of a substrate and a competitive inhibitor and is calculated using an exponential drug concentration pulse curve 160, as shown in FIG. 9. The exponential drug concentration pulse curve is shown in FIG. 9 and the set of input parameters include the substrate concentration (C$_{substrate}$), maximum drug concentration (C$_{max}$), rise time (or time to maximum drug level) (t$_{rise}$), and a drug elimination constant (k$_{drug}$). For example, using variables defined above, the equations used to determine the weighted value for N$_2$ are as follows:

$$N_{2Weighted}(t) = N_2(t) \cdot V_f(t)$$

$$V_f(t) = 1/(1 + ((1 + C_d(t)) \cdot 1/X_{substrate}))$$

$$C_d(t) = B_{Cmax} \cdot e^{kd \cdot t} - B_{Cmax} \cdot e^{ktrise \cdot t}$$

FIG. 10 provides an example of a computer screen shot 170 of the selection of variables to change the graphical representation of the pulse curve to a sinusoidal drug concentration pulse curve by selection of the Sine$^2$ option 172. The sinusoidal drug concentration pulse curve (178) is shown in FIG. 11.

Figure 12A:
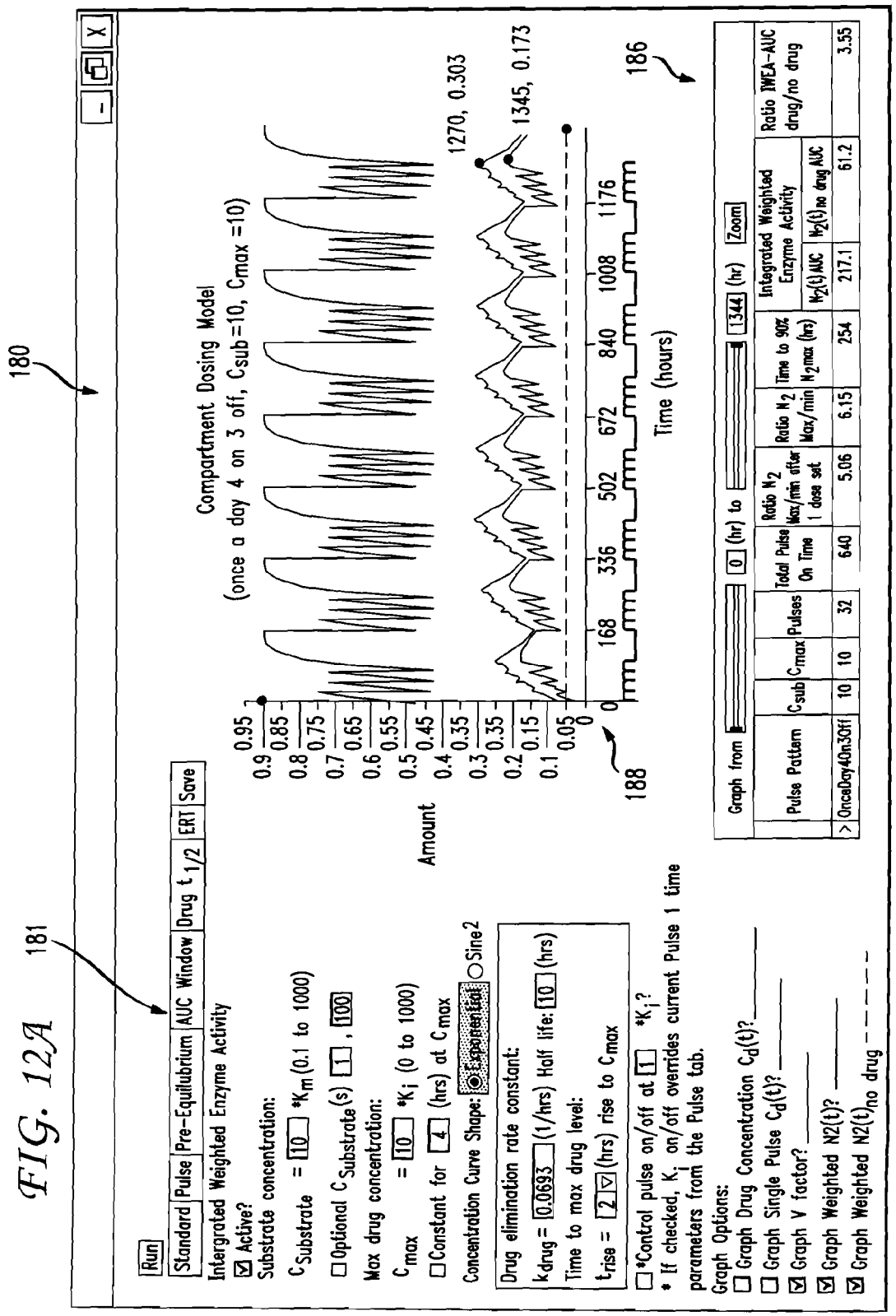
Figure 12C:
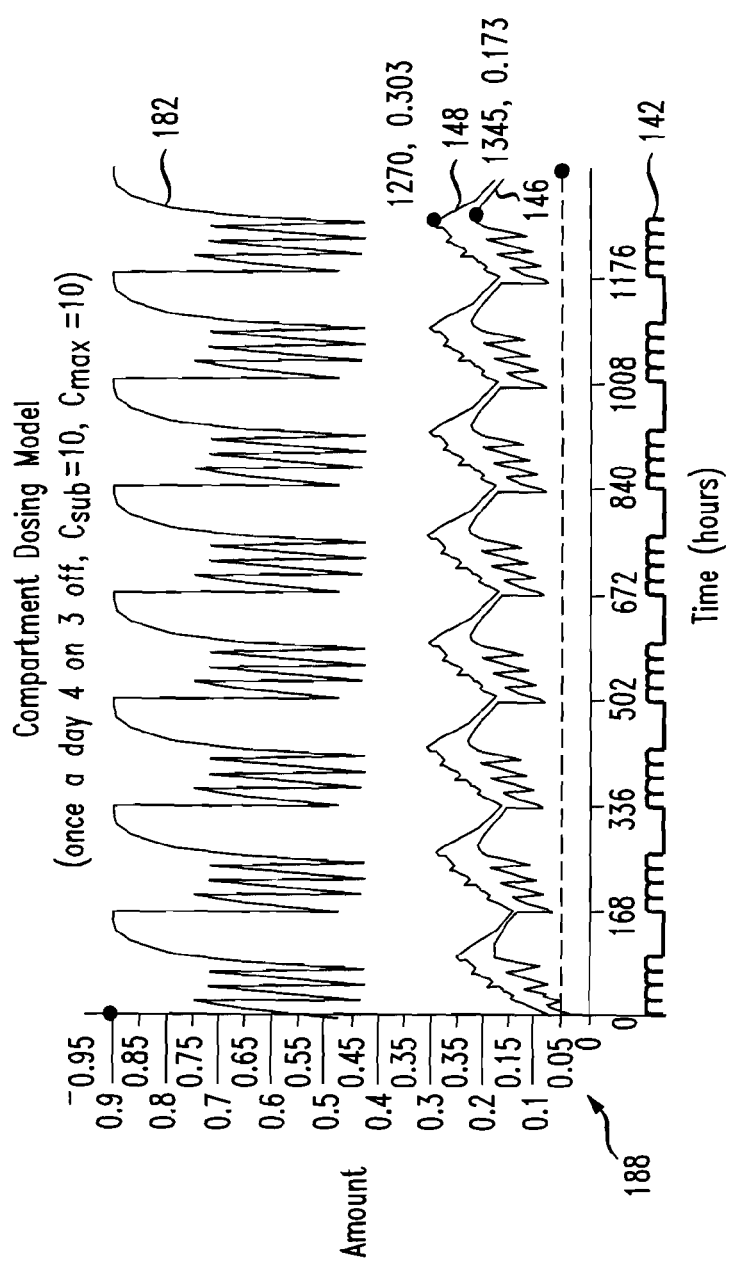

FIGS. 12A-C provide screen shots 180 for evaluating dosing regimens. The variables 181 for determining the weighted values are located on the left side of the screen shot 180 and in FIG. 12B. FIG. 12C shows a graph 188 on the right side of the screen shot 180 with the pulse pattern 142, the weighted N$_2$ dosing model 146, the non-weighted N$_2$ dosing model 148, and the calculated V factor 182. A calculated V factor result chart 186 is also provided in FIG. 12C to show values corresponding to the drug dosing model described in the graph 188.

Figure 14A:
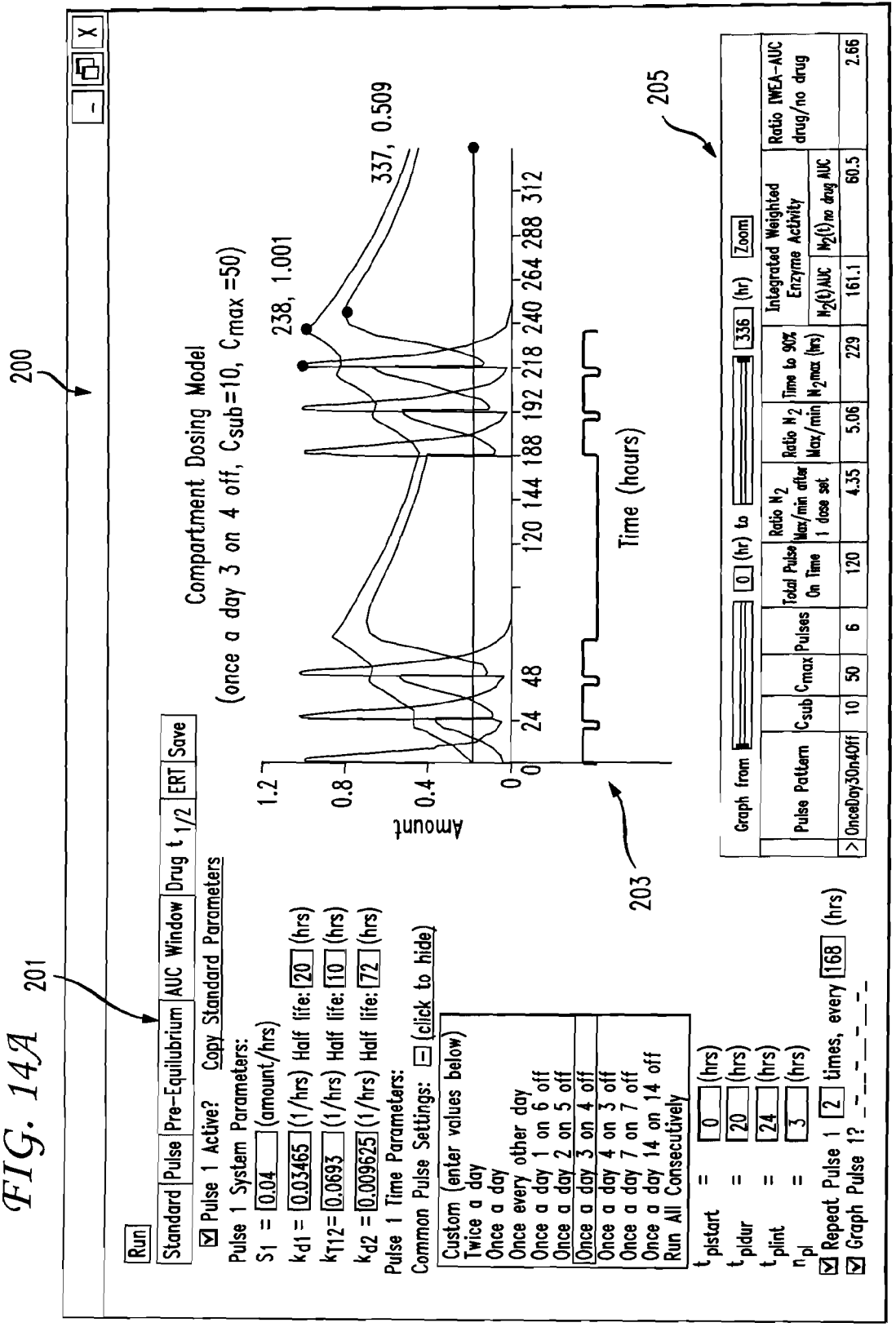
Figure 14C:
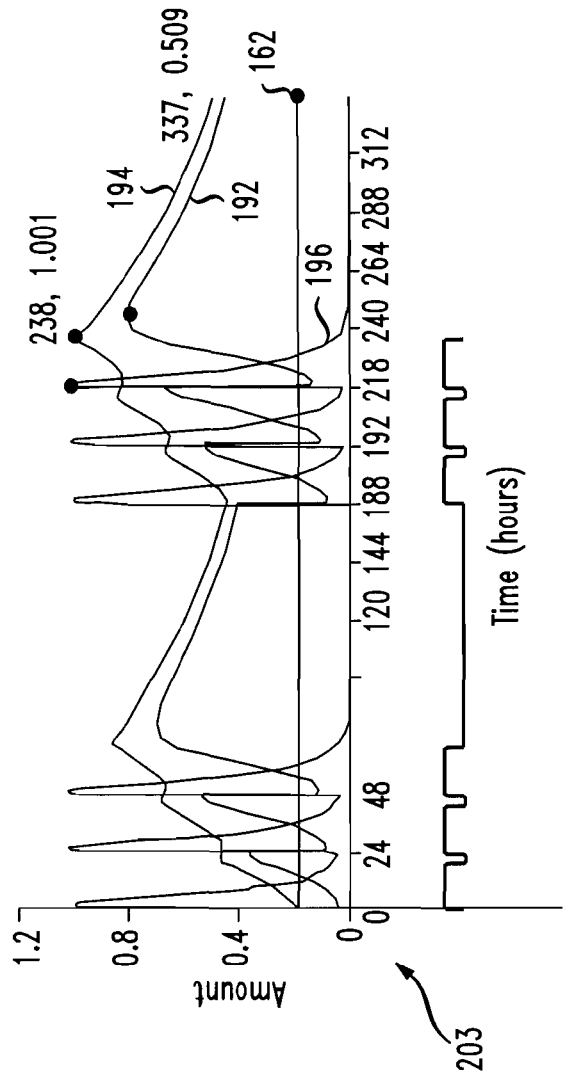

FIGS. 13, 14A-C, and 15A-C provide screenshots 190, 200, and 210 of the weighted 192 and non-weighted 194 enzyme amounts for biocompartment two 34 and the calculated drug concentration curve 196, which is used in the dosing model to simulate a more realistic pulse shape, using an exponential curve shape. In particular, FIG. 14B (201), provides a view of the active Pulse tab 202 that lists the pulse parameters used in the modeled dosing including the pulse time to start the first pulse (t$_{p1start}$) 74, the duration of each pulse (t$_{p1dur}$) 76 the pulse interval time (t$_{p1int}$) 78, and the number of times the pulse repeats (n$_{p1}$) 80. FIG. 14C shows the corresponding graph 203 and chart 205 for the pulse parameters selected.

Figure 15A:
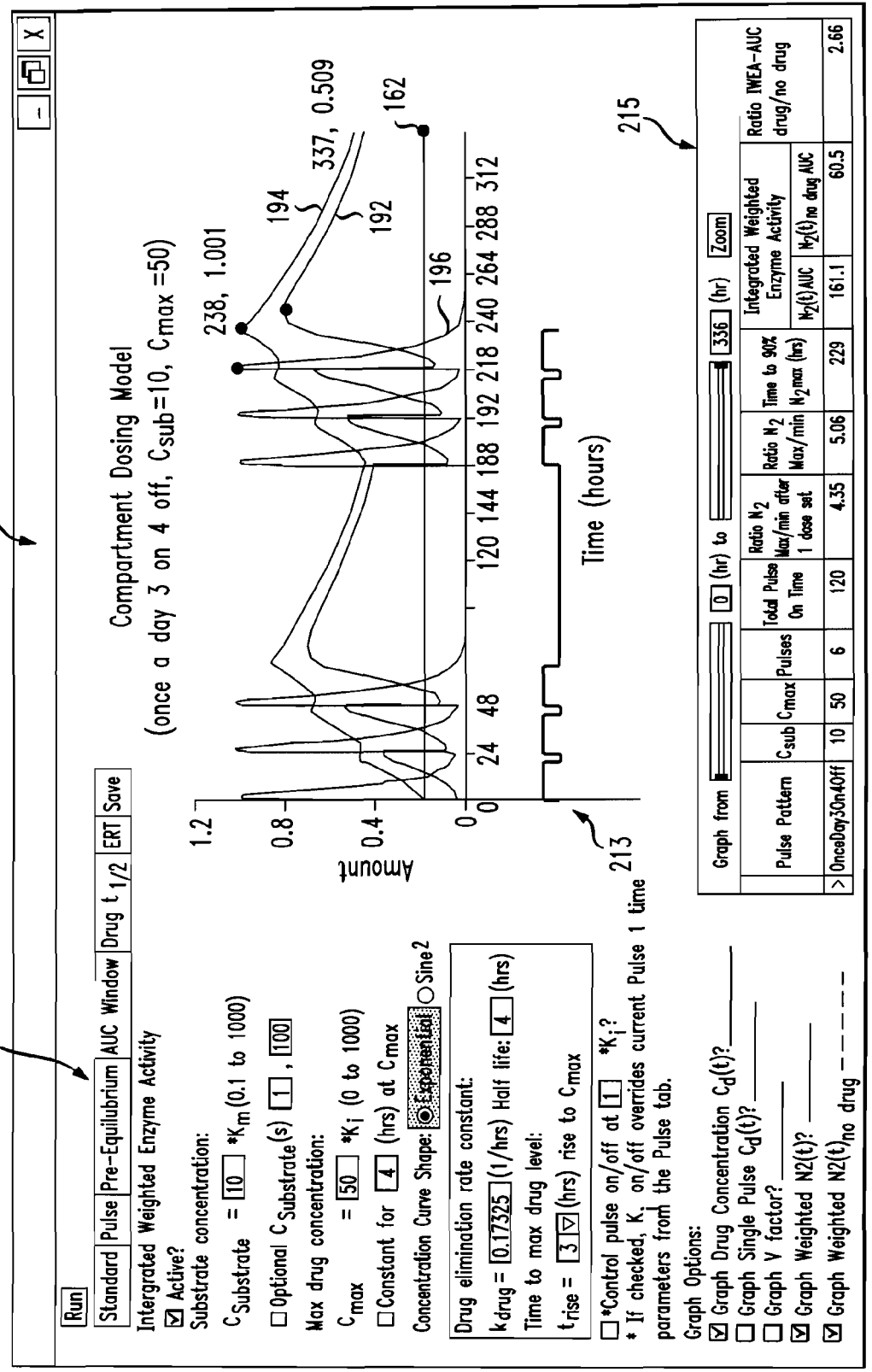
Figure 15C:
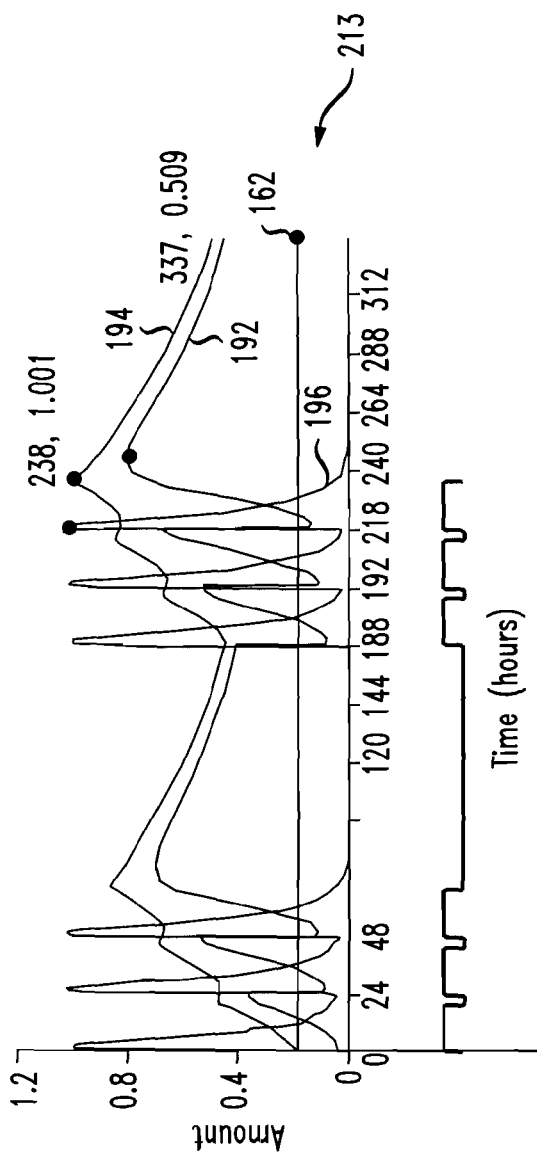

FIG. 15B (211) further provides an active Drug tab 212, that lists the weighted enzyme parameters used in the modeled dosing regimen including substrate concentration (C$_{substrate}$) 150, maximum drug concentration (C$_{max}$) 152, rise time (t$_{rise}$) 156, and a drug elimination constant (k$_{drug}$) 154. FIG. 15C provides the corresponding graph 213 and chart 215 for use in evaluating the dosing regimen.

Figure 16:
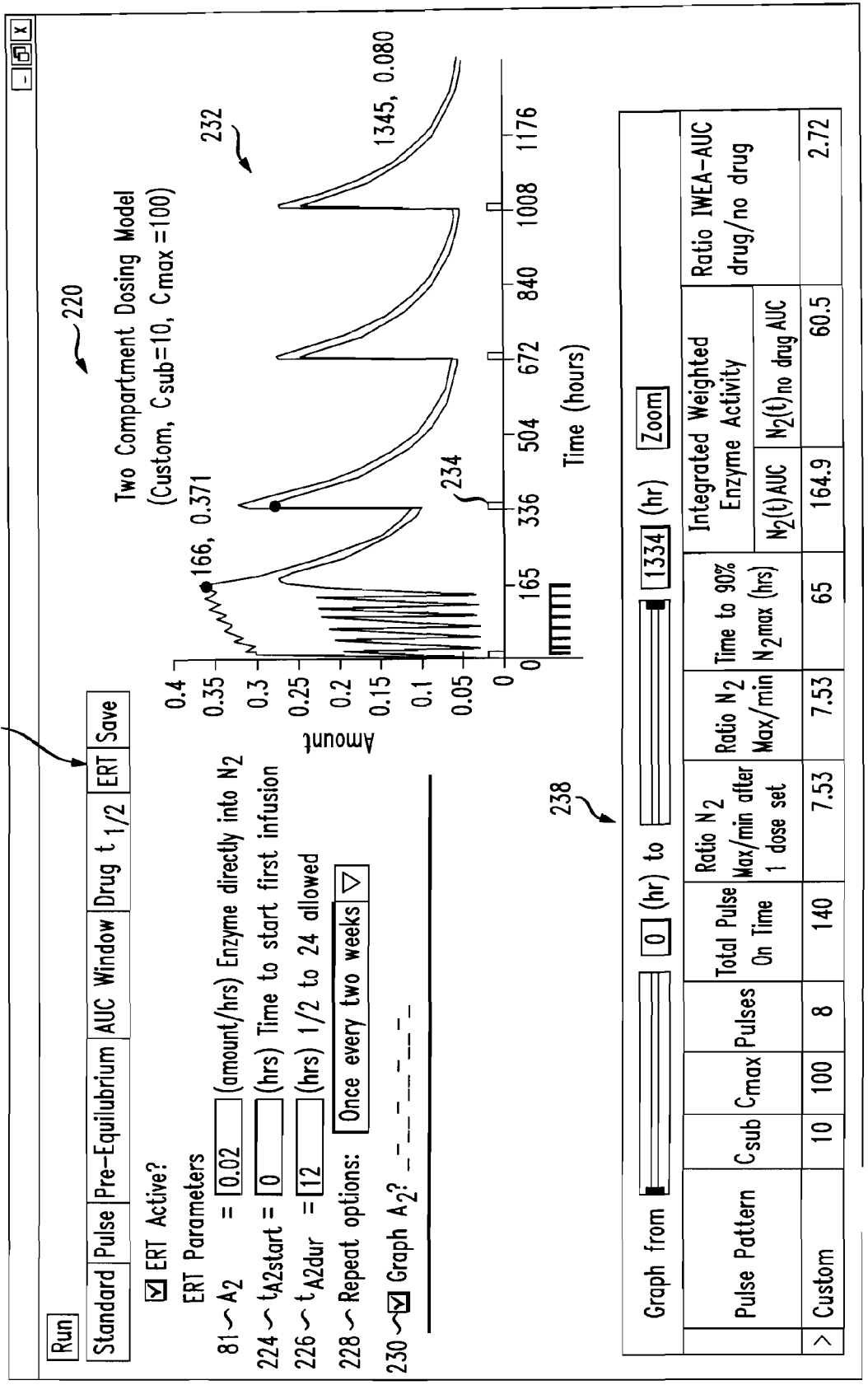
FIG. 16 provides a computer screen shot of the present invention with a set of input parameters and a graphical depiction of the enzyme amounts and a pulse curve with the addition of Enzyme Replacement Therapy.

FIG. 16 provides a computer screen shot 220 of the ERT tab 222 that lists the ERT parameters used to model dosing that includes a constant rate of enzyme (A$_2$) 81 to enter directly into biocompartment 2, the start time for the first infusion/pulse of ERT (t$_{A2start}$) 224, the duration in hours of the ERT (t$_{A2dur}$) 226, and how often the ERT is repeated 228 (the default is once every two weeks). The user can activate the ERT model by checking the "ERT Active" checkbox 230. If ERT is active, the pulses are shown as green rectangles 234 on a graph 232 that appears on the right side of the screen shot 220. The graph 232 further shows concentration of the enzymes in the biocompartment two 38, specifically, weighted N$_2$ (146) and non-weighted N$_2$ (148). Additional details regarding the ERT effects on the concentration of the compartments may be found in the chart 238 below the graph 232. If ERT is inactive, the concentration of the compartments is determined as described above with respect to FIGS. 6-15.

Additionally, the method of the present invention not only may be used to model multiple biocompartment dosing, but also may used to model a single compartment by zeroing out variables. Therefore, conventional dosing with no inhibitors may be modeled with the present method, and standard PK situations by zeroing out the variables associated with pulse patterns.

It will be appreciated that the present invention has been described herein with reference to certain preferred or exemplary embodiments. The preferred or exemplary embodiments described herein may be modified, changed, added to or deviated from without departing from the intent, spirit and scope of the present invention, and it is intended that all such additions, modifications, amendment and/or deviations be included within the scope of the following claims.

What is claimed is:

1. A method for modeling a dosing regimen for a medicament, the method comprising:

providing a system including at least two biocompartments selected from the group consisting of intracellular and extracellular regions;

determining, by a processing device, steady state levels in each of said at least two biocompartments by assigning variables to represent a protein production rate of at least one protein in one of said at least two biocompartments, a degradation rate constant of said at least one protein for each of said at least two biocompartments, and a transport rate constant of said at least one protein between said at least two biocompartments using a set of equations;

modifying, by the processing device, values of said assigned variables in said set of equations to use said set of equations to calculate an amount of said at least one protein in one of said at least two biocompartments to which said at least one protein is being transported, as a function of time, said set of equations reflecting selected characteristics of said at least one protein and one or more drug pulse parameters, said one or more drug pulse parameters include a start time, a duration, an interval time, a number of pulses, an amount of drug, and a number of times settings are repeated;

calculating, by the processing device, a weighted value of said at least one protein in said one of said at least two biocompartments to which said at least one protein is being transported, wherein said weighted value is a result of multiplying a calculated factor by an amount of said at least one protein in said one of said at least two biocompartments to which said at least one protein is being transported, said calculated factor being determined using a drug concentration pulse curve and a set of input parameters including a substrate concentration, a maximum drug concentration, a rise time, and a drug elimination half-life, said drug concentration pulse curve and said set of input parameters associated with a drug;

integrating, by the processing device, said weighted value over a time period to determine a weighted area-under a curve associated with said integrating said weighted value;

calculating, by the processing device, a non-drug value of said at least one protein in said one of said at two biocompartments to which said at least one protein is being transported, wherein said non-drug value is an amount of said at least one protein in said one of said at least two biocompartments to which said at least one protein is being transported without addition of said drug;

integrating, by the processing device, said non-drug value over said time period to find a non-drug area under a curve associated with said integrating of said non-drug value; and evaluating, by the processing device, one or more dosing regimens by comparing said weighted area and said non-drug area of said at least one protein in said one of said at least two biocompartments to which said at least one protein is being transported over said time period to determine a net effect of said drug over said time period.

2. The method of claim 1, wherein said weighted value of said at least one protein in said one of said at least two biocompartments to which said at least one protein is being transported is graphically displayed using one or more of a line graph and a bar chart.

3. The method of claim 1, wherein said protein production rate is graphically displayed using one or more of a line graph and a bar chart.

4. The method of claim 3, wherein said graphically displayed protein production rate shows said protein production rate in each of said at least two biocompartments being run to steady state levels.

5. The method of claim 1, wherein said drug concentration pulse curve is graphically displayed based on said one or more drug pulse parameters.

6. The method of claim 1, wherein said at least one protein comprises an enzyme.

7. The method of claim 6, wherein said enzyme is coupled to a substrate to form a pair.

8. The method of claim 7, wherein said pair is selected from the group consisting of: enzyme alpha galactosidase A and substrate globotriaosylceramide; enzyme glucocerebrosidase and substrate glucocerebroside; and enzyme acid maltase and substrate glycogen.

9. The method of claim 1, wherein said one or more drug pulse parameters further include an Enzyme Replacement Therapy (ERT) enzyme, said ERT enzyme being added to said one of said at least two biocompartments to which said at least one protein is being transported at an ERT interval time.

10. A system for modeling a dosing regimen of a medicament, the system comprising:

a display device;

a data store comprising a plurality of values for modeling a dosing regime of a medicament; and a service delivery device operatively connected to said display device and said data store, said service delivery device including a processor and a memory for storing instructions that, in response to receiving a request to model the dosing regimen of a medicament, causes the processor to:

provide a system including at least two biocompartments selected from the group consisting of intracellular and extracellular regions;

determine steady state levels in each of said at least two biocompartments by assigning variables to represent a protein production rate of at least one protein in one of said at least two biocompartments, a degradation rate constant of said at least one protein for each of said at least two biocompartments, and a transport rate constant of said at least one protein between said at least two biocompartments using a set of equations;

modify values of said assigned variables in said set of equations to use said set of equations to calculate an amount of said at least one protein in one of said at least two biocompartments to which said at least one protein is being transported, as a function of time, said set of equations reflecting selected characteristics of said at least one protein and one or more drug pulse parameters, said one or more drug pulse parameters include a start time, a duration, an interval time, a number of pulses, an amount of drug, and a number of times settings are repeated;

calculate a weighted value of said at least one protein in said one of said at least two biocompartments to which said at least one protein is being transported, wherein said weighted value is a result of multiplying a calculated factor by an amount of said at least one protein in said one of said at least two biocompartments to which said at least one protein is being transported, said calculated factor being determined using a drug concentration pulse curve and a set of input parameters including a substrate concentration, a maximum drug concentration, a rise time, and a drug elimination half-life, said drug concentration pulse curve and a set of input parameters associated with a drug;

integrate said weighted value over a time period to determine a weighted area under a curve associated with integration of said weighed value;

calculate a non-drug value of said at least one protein in said one of said at two biocompartments to which said at least one protein is being transported, wherein said non-drug value is an amount of said at least one protein in said one of said at least two biocompartments to which said at least one protein is being transported without addition of said drug;

integrate said non-drug value over said time period to find a non-drug area under a curve associated with integration of said non-drug value; and evaluate one or more dosing regimens by comparing said weighted area and said non-drug area of said at least one protein in said one of said at least two biocompartments to which said at least one protein is being transported over said time period to determine a net effect of said drug over said time period.

11. The system of claim 10, wherein the memory stores instructions that, in response to receiving the request, cause the processor to graphically display said weighted value of said at least one protein in said one of said at least two biocompartments to which said at least one protein is being transported using one or more of a line graph and a bar chart.

12. The system of claim 10, wherein the memory stores instructions that, in response to receiving the request, cause the processor to graphically display said protein production rate using one or more of a line graph and a bar chart.

13. The system of claim 10, wherein the memory stores instructions that, in response to receiving the request, cause the processor to graphically display said protein production rate of each of said at least two biocompartments being run to steady state levels.

14. The system of claim 10, wherein the memory stores instructions that, in response to receiving the request, cause the processor to graphically display said drug concentration pulse curve based on said one or more drug pulse parameters.

15. The system of claim 10, wherein the memory stores instructions that, in response to receiving the request, cause the processor to graphically display the amount of said at least one protein using one or more of a line graph and a bar chart.

16. The system of claim 10, wherein said at least one protein comprises an enzyme.

17. The system of claim 16, wherein said enzyme is coupled to a substrate to form a pair.

18. The system of claim 17, wherein said pair is selected from the group consisting of: enzyme alpha galactosidase A and substrate globotriaosylceramide; enzyme glucocerebrosidase and substrate glucocerebroside; and enzyme acid maltase and substrate glycogen.

19. The system of claim 10, wherein said one or more drug pulse parameters further include an ERT enzyme, said ERT enzyme being added to said one of said at least two biocompartments to which said at least one protein is being transported at an ERT interval time.

20. A non-transitory computer-readable medium for modeling a dosing regimen for a medicament comprising instructions executable by a computing device that, when applied to the computing device causes the computing device to:

provide a system including at least two biocompartments selected from the group consisting of intracellular and extracellular regions;

determine steady state levels in each of said at least two biocompartments by assigning variables to represent a protein production rate of at least one protein in one of said at least two biocompartments, a degradation rate constant of said at least one protein for each of said at least two biocompartments, and a transport rate constant of said at least one protein between said at least two biocompartments using a set of equations;

modify values of said assigned variables in said set of equations to use said set of equations to calculate an amount of at least one protein in one of said at least two biocompartments to which said at least one protein is being transported, as a function of time, said set of equations reflecting selected characteristics of said at least one protein and one or more drug pulse parameters, said one or more drug pulse parameters include a start time, a duration, an interval time, a number of pulses, an amount of drug, and a number of times settings are repeated;

calculate a weighted value of said at least one protein in said one of said at least two biocompartments to which said at least one protein is being transported, wherein said weighted value is a result of multiplying a calculated factor by an amount of said at least one protein in said one of said at least two biocompartments to which said at least one protein is being transported, said calculated factor being determined using a drug concentration pulse curve and a set of input parameters including a substrate concentration, a maximum drug concentration, a rise time, and a drug elimination half-life, said concentration pulse curve and said set of input parameters associated with a drug;

integrate said weighted value over a time period to determine a weighted area under a curve associated with said integration of said weighted value;

calculate a non-drug value of said at least one protein in said one of said at two biocompartments to which said at least one protein is being transported, wherein said non-drug value is an amount of said at least one protein in said one of said at least two biocompartments to which said at least one protein is being transported without addition of said drug;

integrate said non-drug value over said time period to find a non-drug area under a curve associated with said integration of said non-drug value; and evaluate one or more dosing regimens by comparing said weighted area and said non-drug area of said at least one protein in said one of said at least two biocompartments to which said at least one protein is being transported over said time period to determine a net effect of said drug over said time period.

* * * * *